(12) United States Patent
Scarborough et al.

(10) Patent No.: US 7,189,733 B2
(45) Date of Patent: Mar. 13, 2007

(54) COMPOSITIONS AND METHODS FOR INHIBITING TGF-β

(75) Inventors: Robert M. Scarborough, Half Moon Bay, CA (US); Anjali Pandey, Fremont, CA (US); Meenakshi S. Venkatraman, Foster City, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 301 days.

(21) Appl. No.: 10/795,538

(22) Filed: Mar. 8, 2004

(65) Prior Publication Data

US 2004/0204431 A1 Oct. 14, 2004

Related U.S. Application Data

(60) Provisional application No. 60/454,164, filed on Mar. 12, 2003.

(51) Int. Cl.
*A61K 31/517* (2006.01)
*A61K 31/44* (2006.01)
*C07D 471/02* (2006.01)

(52) U.S. Cl. .................. 514/266.2; 514/303; 544/284; 546/119

(58) Field of Classification Search ............. 514/266.2, 514/303; 544/284; 546/119
See application file for complete search history.

(56) References Cited

U.S. PATENT DOCUMENTS

| | | | |
|---|---|---|---|
| 5,223,501 A * | 6/1993 | Chakravarty et al. .......... 514/81 |
| 5,571,828 A * | 11/1996 | Strupczewski et al. ..... 514/373 |
| 6,184,226 B1 | 2/2001 | Chakravarty et al. .. 514/266.22 |
| 6,225,318 B1 * | 5/2001 | Sobolov-Jaynes et al. ....................... 514/266.2 |
| 6,277,989 B1 | 8/2001 | Chakravarty et al. ....... 544/393 |
| 6,476,031 B1 | 11/2002 | Chakravarty et al. ....... 514/249 |
| 2002/0161010 A1 | 10/2002 | Chakravarty et al. ....... 514/249 |

FOREIGN PATENT DOCUMENTS

| WO | WO 00/12497 A2 | 3/2000 |
|---|---|---|
| WO | WO 03/097615 A1 | 11/2003 |
| WO | WO 04/010929 A2 | 2/2004 |

OTHER PUBLICATIONS

Chemical Abstracts Registry File, Registry No. 685134-74-1 (see attached).

* cited by examiner

*Primary Examiner*—James O. Wilson
*Assistant Examiner*—Tamthom N. Truong
(74) *Attorney, Agent, or Firm*—Millennium Pharmaceutical Inc.

(57) ABSTRACT

This invention provides compounds that are useful for treating patients having a TGF-β-mediated disease, particularly an ALK5-mediated disease. The compounds are represented by formula I:

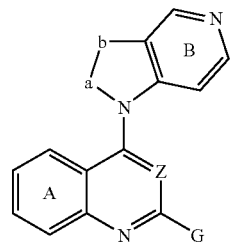

wherein: a-b is $CH_2CH_2$, $CH_2CH_2CH_2$, $CH=CH$, $CH=N$, or $N=CH$; Z is N or C—F; and G is $C_{1-6}$ aliphatic or a phenyl, naphthyl, or 5-6 membered heteroaryl ring.

7 Claims, No Drawings

COMPOSITIONS AND METHODS FOR INHIBITING TGF-β

This application claims the benefit of Provisional Application No. 60/454,164 filed Mar, 12, 2003.

FIELD OF INVENTION

This invention relates to novel compounds and methods for inhibiting the transforming growth factor (TGF)-β signaling pathway. The compounds and methods are particularly useful for treating cardiovascular disease.

BACKGROUND OF THE INVENTION

TGF-β1 belongs to a large super-family of multifunctional polypeptide factors. The TGF-β family includes three genes, TGFβ1, TGFβ2 and TGFβ3, which are pleiotropic modulators of cell growth and differentiation, embryonic and bone development, extracellular matrix formation, hematopoiesis, immune and inflammatory responses. These genes have high homology with one another. In mammals, the TGFβ super-family includes various TGFβ genes, as well as the embryonic morphogenes, such as the family of the activins, inhibins, "Mullerian Inhibiting Substance", and bone morphogenic protein (BMP). Roberts and Sporn, The Transforming Growth Factor-βs in Peptide Growth Factors and Their Receptors. I. *Handbook of Experimental Pharmacology*, vol. 95/I, Springer-Verlag, Berlin, 419–472 (1990). Each member of the TGF-β family exerts a wide range of biological effects on a large variety of cell types, e.g., they regulate cell growth, morphogenesis, differentiation, matrix production and apoptosis. Lagna et al., *Nature*, 383:832–836 (1996). TGF-β acts as a growth inhibitor for many cell types and appears to play a central role in the regulation of embryonic development, tissue regeneration, immuno-regulation, as well as in fibrosis and carcinogenesis. TGFβ1 inhibits the growth of many cell types, including epithelial cells, but stimulates the proliferation of various types of mesenchymal cells.

In addition, TGFβs induce the synthesis of extracellular matrix (ECM) proteins, modulate the expression of matrix proteinases and proteinase inhibitors and change the expression of integrins. ECM is a dynamic superstructure of self aggregating macromolecules including fibronectin, collagen and proteoglycan. ECM is the chief pathologic feature of fibrotic diseases. ECM disorder has been proposed to play a central role in pathogenesis disorders such as hypertensive vascular disease and diabetic renal disease. Sato et al., *Am. J. Hypertens.*, 8:160–166 (1995); Schulick et al., *Proc. Natl. Acad. Sci.*, 95:6983–6988 (1988). Moreover, TGFβs are expressed in large amounts in many tumors. Derynck, *Trends Biochem. Sci.*, 19:548–553, (1994). This strong occurrence in neoplastic tissues could indicate that TGFβs are strategic growth/morphogenesis factors which influence the malignant properties associated with the various stages of the metastatic cascade. TGFβs inhibit the growth of normal epithelial and relatively differentiated carcinoma cells, whereas undifferentiated tumor cells which lack many epithelial properties are generally resistant to growth inhibition by TGFβs (Hoosein et al., Exp. Cell. Res. 181: 442–453(1989); Murthy et al., *Int'l J. Cancer,* 44:110–115 (1989). Furthermore TGFβ1 may potentiate the invasive and metastatic potential of a breast adenoma cell line (Welch et al., *Proc. Natl. Acad. Sci.*, 87:7678–7682(1990), which indicates a role of TGFβ1 in tumor progression. The molecular mechanisms underlying the effect of TGFβs during tumor cell invasion and metastasization do, however, require further explanation.

The cellular effects of TGFβ are exerted by ligand-induced hetero-oligomerization of two distantly related type I and type II serine/threonine kinase receptors, TGFβR-I and TGFβ R-II, respectively. Lin and Lodish, *Trends Cell Biol.*, 11:972–978. (1993); Massague and Weis-Garcia, *Cancer Surv.*, 27:41–64(1996); ten Dijke et al., *Curr. Opin. Cell Biol.*, 8:139–145 (1996). The two receptors, both of which are required for signaling, act in sequence; TGFβR-I is a substrate for the constitutively active TGFβR-II kinase. Wrana et al., *Nature*, 370:341–347 (1994); Wieser et al., *EMBO J.*, 14:2199–2208 (1995). Upon TGFβ1 binding, the type II receptor phosphorylates threonine residues in the GS domain of ligand occupied type I receptor or activin-like kinase (ALK5), which results in activation of type I receptors. The TGFβ1 type I receptor in turn phosphorylates Smad2 and Smad3 proteins which translocate to the nucleus and mediate intracellular signaling. The inhibition of ALK5 phosphorylation of Smad3 will reduce TGFβ1 induced extracellular matrix production. Krettzchmar et al., *Genes Dev.*, 11: 984–995 (1997); Wu et al., *Mol. Cell. Biol.*, 17:2521–2528 (1997); U.S. Pat. No. 6,465,493.

TGFβ is a powerful and essential immune regulator in the vascular system capable of modulating inflammatory events in both leuko and vascular endothelial cells. Shull et al., *Nature*, 359:693–699 (1992). It is also involved in the pathogenesis of chronic vascular diseases such as atherosclerosis and hypertension. Grainger & Metcalfe et al., *Bio. Rev. Cambridge Phil. Soc.*, 70:571–596 (1995); Metcalfe et al., *J. Human Hypertens.*, 9:679 (1995).

Genetic studies of TGFβ-like signaling pathways in *Drosophila and Caenorhabditis elegans* have led to the identification of mothers against dpp (Mad). Sekelsky et al., *Genetics*, 139:1347–1358 (1995) and sma genes respectively. Savage et al., *Proc. Natl. Acad. Sci. USA*, 93:790–794, (1996). The products of these related genes perform essential functions downstream of TGFβ-like ligands acting via serine/threonine kinase receptors in these organisms. Wiersdorf et al., *Development*, 122:2153–2163 (1996); Newfeld et al., *Development*, 122:2099–2108 (1996); Hoodless et al., *Cell*, 85:489–500 (1996). Vertebrate homologs of Mad and sma have been termed Smads. Derynck et al., *Cell*, 87:173 (1996) or MADR genes. Wrana and Attisano, *Trends Genet.*, 12:493–496 (1996). SMAD proteins have been identified as signaling mediators of TGFβ superfamily. Hahn et al., *Science*, 271:350–353 (1996). Genetic alterations in Smad2 and Smad4/DPC4 have been found in specific tumor subsets, and thus Smads may function as tumor suppressor genes. Hahn et al., *Science*, 271:350–353 (1996); Riggins et al., *Nature Genet.*, 13:347–349 (1996); Eppert et al., *Cell*, 86:543–552 (1996). Smad proteins share two regions of high similarity, termed MH1 and MH2 domains, connected with a variable proline-rich sequence. Massague, *Cell*, 85:947–950 (1996); Derynck and Zhang, *Curr. Biol.*, 6:1226–1229 (1996). The C-terminal part of Smad2, when fused to a heterologous DNA-binding domain, was found to have transcriptional activity. Liu et al., *Nature*, 381:620–623 (1996); Meersseman et al., *Mech. Dev.*, 61:127–140 (1997). The intact Smad2 protein when fused to a DNA-binding domain, was latent, but transcriptional activity was unmasked after stimulation with ligand. Liu et al., supra.

TGFβ initiates an intracellular signaling pathway leading ultimately to the expression of genes that regulate the cell cycle, control proliferative responses, or relate to extracellular matrix proteins that mediate outside-in cell signaling, cell adhesion, migration and intercellular communication.

There exists a need for effective therapeutic agents for inhibiting TGFβ activity, as well as for inhibiting the phosphorylation of smad2 or smad3 by TGFβ type I or activin-like kinase (ALK5) receptor and for preventing and treating disease states mediated by the TGFβ signaling pathway in mammals. In particular, there continues to be a need for compounds that selectively inhibit TGFβ, especially the ALK5 receptor.

DESCRIPTION OF THE INVENTION

The present invention provides compounds that are useful for treating patients having a TGFβ-mediated disease, particularly an ALK5-mediated disease. The compounds are represented by formula I:

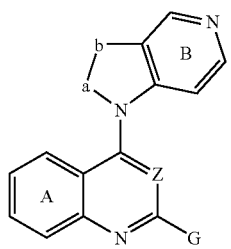

I or a pharmaceutically acceptable salt thereof, wherein:

a-b is $CH_2CH_2$, $CH_2CH_2CH_2$, CH=CH, CH=N, or N=CH, wherein each hydrogen is optionally replaced by a $C_{14}$ aliphatic group;

Z is N or C—F;

G is $C_{1-6}$ aliphatic or a phenyl, naphthyl, or 5–6 membered heteroaryl ring having 1–ring heteroatoms selected from nitrogen, sulfur or oxygen, wherein G is optionally substituted by 1–3 $R^5$;

Ring A is optionally substituted by 1–3 $R^1$;

Ring B is optionally substituted by 1–2 $R^6$ at a position ortho to the ring nitrogen and is optionally substituted by $R^7$ at the position meta to the ring nitrogen;

each $R^1$ is independently selected from —$R^2$, -T-$R^2$, or —V-T-$R^2$;

each $R^2$ is independently selected from $C_{1-3}$ aliphatic, hydroxy, —$N(R^3)_2$, halo, cyano, —$OR^4$, —$C(O)R^4$, —$CO_2R^4$, —$SR^4$, —$S(O)R^4$, —$S(O)_2R^4$, —$N(R^3)C(O)R^4$, —$N(R^3)CO_2R^4$, —$N(R^3)SO_2R^4$, —$C(O)N(R^3)_2$, —$SO_2N(R^3)_2$, —$N(R^3)C(O)N(R^3)_2$, —$OC(O)R^4$, phenyl, 5–6 membered heterocyclyl or 5–6 membered heteroaryl;

each T is independently a $C_{1-5}$ alkylidene that is optionally interrupted by —O—, —C(O)—, —S—, —S(O)—, —$S(O)_2$—, or —$N(R^3)$—;

each V is independently selected from —O—, —S—, —S(O)—, —$S(O)_2$— —C(O)—, —$N(R^3)$—, —$N(R^3)C(O)$—, or —$N(R^3)C(O)_2$—, —$N(R^3)S(O)_2$—, —C(O)N($R^3$)—, —$S(O)_2N(R^3)$—, —$N(R^3)C(O)N(R^3)$—, or —OC(O)—;

each $R^3$ is independently selected from hydrogen, $C_{1-6}$ aliphatic, —$C(O)R^4$, —$C(O)_2R^4$, —$SO_2R^4$, or two $R^3$ on the same nitrogen together with their intervening nitrogen form a 5–6 membered heterocyclyl or heteroaryl ring having 1–3 ring heteroatoms selected from nitrogen, oxygen or sulfur;

each $R^4$ is independently selected from a $C_{1-6}$ aliphatic group, phenyl or a 5–6 membered heteroaryl or heterocyclyl having 1–3 ring heteroatoms selected from nitrogen, oxygen or sulfur;

each $R^5$ is independently selected from $C_{1-6}$ aliphatic, halo, —OH, —$N(R^3)$ 2, cyano, —$OR^4$, —$C(O)R^4$, —$CO_2R^4$—$SR^4$, —$S(O)R^4$, —$S(O)_2R^4$, —$N(R^3)C(O)R^4$, —$N(R^3)CO_2R^4$, —$N(R^3)SO_2R^4$, —$C(O)N(R^3)_2$, —$SO_2N(R^3)_2$, —$N(R^3)C(O)N(R^3)_2$, —$OC(O)R^4$, —$OC(O)N(R^3)_2$, phenyl, 5–6 membered heterocyclyl or 5–6 membered heteroaryl, or two adjacent $R^5$ on a phenyl, naphthyl or heteroaryl ring are taken together with their intervening atoms to form a 5–6 membered fused ring having 0–2 heteroatoms selected from nitrogen, oxygen or sulfur;

each $R^6$ is independently selected from a $C_{1-4}$ alkyl, $C_{1-4}$ alkoxy, or $C_{14}$ mono- or dialkylamino; and $R^7$ is selected halo, —OH, —$N(R^3)_2$, cyano, —$OR^4$, —$C(O)R^4$-$CO_2R^4$, —$SR^4$, —$S(O)R^4$, —$S(O)_2R^4$, —$N(R^3)C(O)R^4$, —$N(R^3)CO_2R^4$, —$N(R^3)SO_2R^4$, —$C(O)N(R^3)_2$, —$SO_2N(R^3)_2$, —$N(R^3)C(O)N(R^3)_2$, or —$OC(O)R^4$.

The term "aliphatic" as used herein means straight-chain, branched or cyclic $C_1$–$C_{12}$ hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl) alkyl or (cycloalkyl)alkenyl. The terms "alkyl", "alkoxy", "hydroxyalkyl", "alkoxyalkyl", and "alkoxycarbonyl", used alone or as part of a larger moiety, include both straight and branched chains containing one to twelve carbon atoms. The terms "alkenyl" and "alkynyl", used alone or as part of a larger moiety, include both straight and branched chains containing two to twelve carbon atoms. The term "cycloalkyl, used alone or as part of a larger moiety, includes cyclic $C_3$–$C_{12}$ hydrocarbons which are completely saturated or which contain one or more units of unsaturation, but which are not aromatic.

The terms "haloalkyl", "haloalkenyl" and "haloalkoxy", mean alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0–3 heteroatoms selected from oxygen, sulfur or nitrogen, the nitrogen may be N (as in 3,4-dihydro-2-pyrrolyl), NH (as in pyrrolidinyl) or NR+ (as in N-substituted pyrrolidinyl).

The terms "carbocycle", "carbocyclyl", "carbocyclo", or "carbocyclic" as used herein means an aliphatic ring system having three to fourteen members. The terms "carbocycle", "carbocyclyl", "carbocyclo", or "carbocyclic" whether saturated or partially unsaturated, also refers to rings that are optionally substituted. The terms "carbocycle", "carbocyclyl", "carbocyclo", or "carbocyclic" also include aliphatic rings that are fused to one or more aromatic or nonaromatic rings, such as in a decahydronaphthyl or tetrahydronaphthyl, where the radical or point of attachment is on the aliphatic ring.

The term "aryl" used alone or as part of a larger moiety as in "aralkyl", "aralkoxy", or "aryloxyalkyl", refers to aromatic ring groups having five to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heterocycle", "heterocyclyl", or "heterocyclic" as used herein includes non-aromatic ring systems having five to fourteen members, preferably five to ten, in which one or more ring carbons, preferably one to four, are each replaced by a heteroatom such as N, O, or S. Examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Examples of suitable substituents on the unsaturated carbon atom of an aryl, heteroaryl, aralkyl, or heteroaralkyl group include a halogen, —R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO$_2$, —CN, —N(R°)$_2$, —NR°C(O)R°, —NR°C(O)N(R°)$_2$, —NR°CO$_2$R°, —NR°NR°C(O)R°, —NR°NR°C(O)N(R°)$_2$, —NR°NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)—N(R°)$_2$, —(CH$_2$)$_y$NHC(O)R°, —(CH$_2$)$_y$NHC(O)CH(V—R°)(R°); wherein each R° is independently selected from hydrogen, a substituted or unsubstituted aliphatic group, an unsubstituted heteroaryl or heterocyclic ring, phenyl (Ph), substituted Ph, —O(Ph), substituted —O(Ph), —CH$_2$(Ph), or substituted —CH$_2$(Ph); y is 0–6; and V is a linker group. Examples of substituents on the aliphatic group or the phenyl ring of R° include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

An aliphatic group or a non-aromatic heterocyclic ring may contain one or more substituents. Examples of suitable substituents on the saturated carbon 20 of an aliphatic group or of a non-aromatic heterocyclic ring include those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen, an unsubstituted aliphatic group or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

Suitable substituents on the nitrogen of a non-aromatic heterocyclic ring include —R+, —N(R+)$_2$, —C(O)R+, —CO$_2$R+, —C(O)C(O)R+, —C(O)CH$_2$C(O)R+, —SO$_2$R+, —SO$_2$N(R+)$_2$, —C(=S)N(R+)$_2$, —C(=NH)—N(R+)$_2$, and —NR+SO$_2$R+; wherein each R+ is independently selected from hydrogen, an aliphatic group, a substituted aliphatic group, phenyl (Ph), substituted Ph, —O(Ph), substituted —O(Ph), CH$_2$(Ph), substituted CH$_2$(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

The term "linker group" or "linker" means an organic moiety that connects two parts of a compound. Linkers are typically comprised of an atom such as oxygen or sulfur, a unit such as —NH—, —CH$_2$—, —C(O)—, —C(O)NH—, or a chain of atoms, such as an alkylidene chain. The molecular mass of a linker is typically in the range of about 14 to 200, preferably in the range of 14 to 96 with a length of up to about six atoms. Examples of linkers include a saturated or unsaturated $C_{1-6}$ alkylidene chain which is optionally substituted, and wherein one or two saturated carbons of the chain are optionally replaced by —C(O)—, —C(O)C(O)—, —CONH—, —CONHNH—, —$CO_2$—, —OC(O)—, —$NHCO_2$—, —O—, —NHCONH—, —OC(O)NH—, —NHNH—, —NHCO—, —S—, —SO—, —$SO_2$—, —NH—, —$SO_2$NH—, or —$NHSO_2$—.

The term "alkylidene chain" refers to an optionally substituted, straight or branched carbon chain that may be fully saturated or have one or more units of unsaturation. The optional substituents are as described above for an aliphatic group.

A combination of substituents or variables is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen atom by a deuterium or tritium, or the replacement of a carbon by a $^{13}C$- or $^{14}C$-enriched carbon are within the scope of this invention.

Ring B of formula I is preferably unsubstituted or substituted by one or two $R^6$ (ortho to the nitrogen) where $R^6$ is methyl, methoxy, amino or alkylamino where the alkyl moiety is substituted or unsubstituted.

When Z is C—F, Ring A forms part of a quinoline ring system and when Z is nitrogen, Ring A forms part of a quinazoline ring system. When Ring A is substituted, it is preferably substituted at positions 6 and/or 7 of the quinoline or quinazoline ring system.

The G moiety of formula I is preferably a substituted or unsubstituted phenyl, naphthyl, $C_{3-6}$ alkyl or cycloalkyl, pyridyl, thienyl or furanyl. Preferred $R^5$ substituents on G include halo, amino, cyano, hydroxy, $C_{1-6}$ alkoxy, $C_{1-6}$ alkyl, $C_{3-6}$ cycloalkyl, haloalkyl, $C_{1-6}$ alkylthio, mono- or dialkylamino, aminocarbonyl, mono- or dialkylaminocarbonyl, $C_{1-6}$ alkylcarbonyl, $C_{1-6}$ alkylsulfonyl, $C_{1-6}$ alkoxycarbonyl, $C_{1-6}$ alkoxycarbonylamino, $C_{1-6}$ alkylcarbonyloxy, $C_{1-6}$ alkylsulfonylamino, mono- or dialkylaminosulfonyl, mono- or dialkylaminocarbonylamino, or two adjacent $R^5$ are taken together with their intervening atoms to form a fused 5–6 membered ring having 0–2 ring heteroatoms. When Z is nitrogen and G is a substituted aryl or heteroaryl ring, it is advantageous to have an $R^5$ substituent at the 2-position of the G ring relative to its attachment to the quinazoline portion of the compound. When Z is C—F and G is a substituted aryl or heteroaryl ring, the $R^5$ substituent is preferably at the 3-position of the G ring relative to the quinoline portion of the compound.

On Ring A, $R^1$ is selected from —$R^2$, -T-$R^2$ or —V-T-$R^2$. A preferred $R^2$ is halo, $C_{1-3}$ aliphatic, —$N(R^3)_2$, or —$OR^4$. A preferred T is a $C_{1-4}$ alkylidene, more preferably a $C_{2-3}$ alkylidene. A preferred V is —O— or —$N(R^3)$—.

One embodiment of this invention relates to a compound of formula I where a-b is CH═CH, represented by formula II:

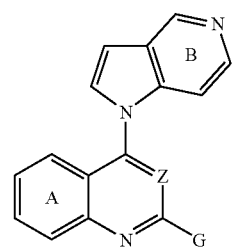

II

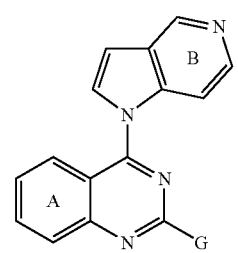

II-a

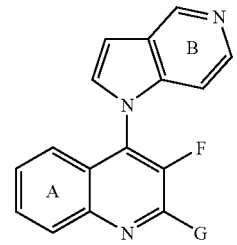

II-b where Z is nitrogen (formula II-a) or C—F (formula II-b) and G is as described above.

Another embodiment of this invention relates to a compound of formula I where a-b is CH═N, represented by formula III:

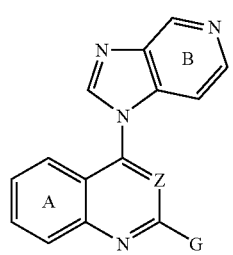

III

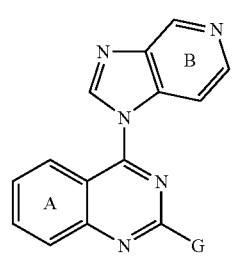

III-a

III-b

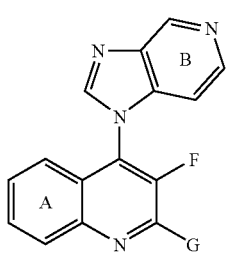

where Z is nitrogen (formula III-a) or C—F (formula III-b) and G is as described above.

Another embodiment of this invention relates to a compound of formula I where a-b is N=CH, represented by formula IV:

IV

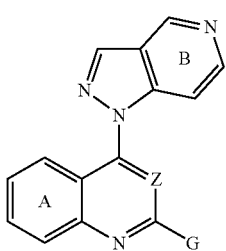

IV-a

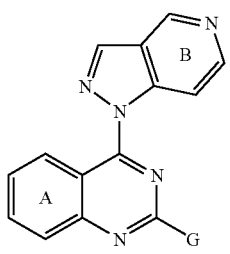

IV-b

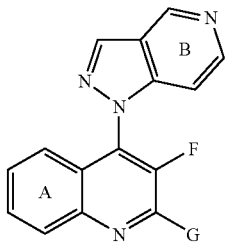

where Z is nitrogen (formula IV-a) or C—F (formula IV-b) and G is as described above.

Another embodiment of this invention relates to a compound of formula I where a-b is $CH_2$—$CH_2$, represented by formula V:

V

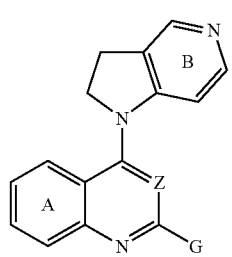

V-a

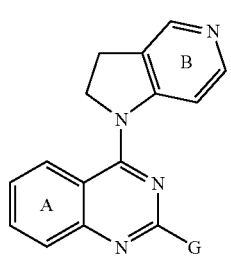

V-b

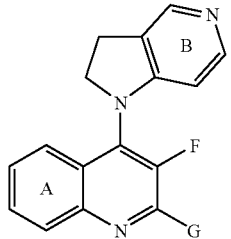

where Z is nitrogen (formula V-a) or C—F (formula V-b) and G is as described above.

Another embodiment of this invention relates to a compound of formula I where a-b is $CH_2$—$CH_2$—$CH_2$, represented by formula VI:

VI

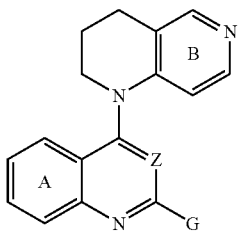

VI-a

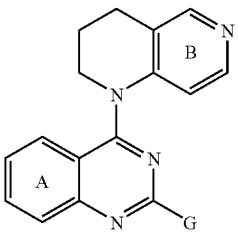

VI-b

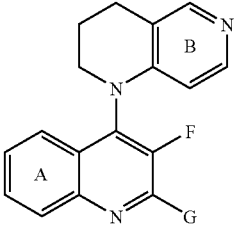

where Z is nitrogen (formula VI-a) or C—F (formula VI-b) and G is as described above.

One embodiment provides compounds of formula I that have at least one feature, and more preferably all of the features, selected from the group consisting of:
(a) G is a phenyl, naphthyl or heteroaryl ring that is unsubstituted or substituted by 1–2 $R^5$ groups;

(b) Ring A is unsubstituted or substituted by 1–2 $R^1$ groups at positions 6 and/or 7 of the quinoline or quinazoline ring system;

(c) Ring B is unsubstituted or substituted by an $R^6$ group where $R^6$ is methyl, amino, or methylamino;

(d) $R^1$ is $R^2$, T-$R^2$ or V-T-$R^3$ where $R^2$ is halo, $C_{1-3}$ aliphatic, $C_{1-3}$ alkoxy, amino, $C_{1-6}$ mono- or dialkylamino, T is a $C_{1-4}$ alkylidene that is optionally interrupted by —C(=O)—, V is —O— or —N($R^3$)—, and $R^3$ is hydrogen or methyl; and (e) $R^5$ is halo, $C_{1-6}$ alkoxy, $C_{1-6}$ alkyl, $C_{3-6}$ cycloalkyl, haloalkyl, $C_{1-6}$ alkylthio, mono- or dialkylamino, aminocarbonyl, mono- or dialkylaminocarbonyl, $C_{1-6}$ alkylcarbonyl, $C_{1-6}$ alkylsulfonyl, $C_{1-6}$ alkoxycarbonyl, $C_{1-6}$ alkoxycarbonylamino, $C_{1-6}$ alkylcarbonyloxy, $C_{1-6}$ alkylsulfonylamino, mono- or dialkylaminosulfonyl, mono- or dialkylaminocarbonylamino, or two adjacent $R^5$ are taken together with their intervening atoms to form a fused 5–6 membered ring having 0–2 ring heteroatoms.

Particular aspects of this embodiment relate to compounds of each of formulae II–VI that have at least one feature, and more preferably all of the features, selected from the group consisting of (a)–(e) above.

Another embodiment provides compounds of formula I that have at least one feature, and more preferably all of the features, selected from the group consisting of:

(a) G is a phenyl ring that is unsubstituted or substituted by 1–2 $R^5$ groups;

(b) Ring A is unsubstituted or substituted by 1–2 $R^1$ groups at positions 6 and/or 7 of the quinoline or quinazoline ring system;

(c) Ring B is unsubstituted or substituted by an $R^6$ group where $R^6$ is methyl, amino, or methylamino;

(d) $R^1$ is $R^2$, T-$R^2$ or V-T-$R^3$ where $R^2$ is halo, $C_{1-3}$ aliphatic, —N($R^3$)$_2$, or —O$R^4$, T is a $C_{1-3}$ alkylidene, V is —O— or —N($R^3$)—, and $R^3$ is hydrogen or methyl; and (e) $R^5$ is halo, amino, cyano, hydroxy, $C_{1-6}$ alkoxy, $C_{1-6}$ alkyl, $C_{3-6}$ cycloalkyl, haloalkyl, $C_{1-6}$ alkylthio, mono- or dialkylamino, aminocarbonyl, mono- or dialkylaminocarbonyl, $C_{1-6}$ alkylcarbonyl, $C_{1-6}$ alkylsulfonyl.

Particular aspects of the above embodiment relate to compounds of each of formulae II–VI that have at least one feature, and more preferably all of the features, selected from the group consisting of (a)–(e) above.

Examples of specific compounds of this invention are shown in Table I below.

TABLE 1

| | |
|---|---|
| 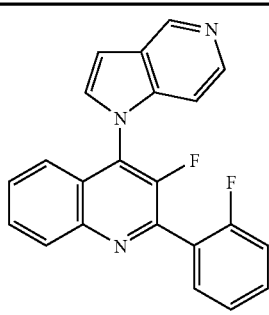 | 1 |
| 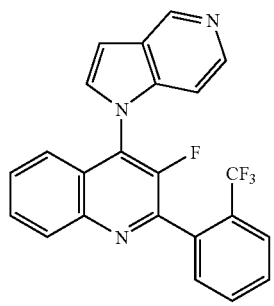 | 2 |
| 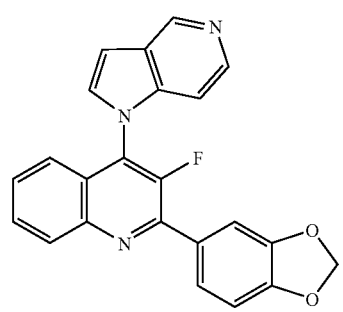 | 3 |
| 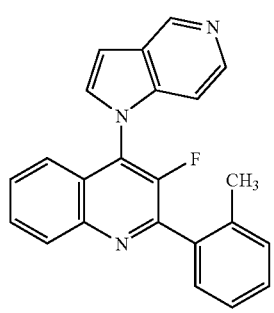 | 4 |
| 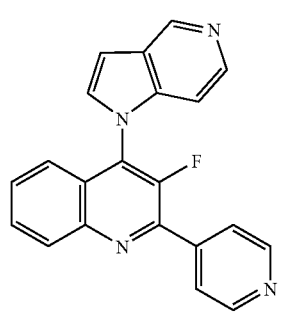 | 5 |
| 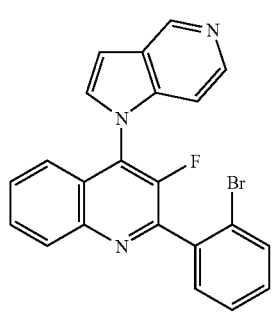 | 6 |

TABLE 1-continued

| | |
|---|---|
| 7 | 12 |
| 8 | 13 |
| 9 | 14 |
| 10 | 15 |
| 11 | 16 |

TABLE 1-continued
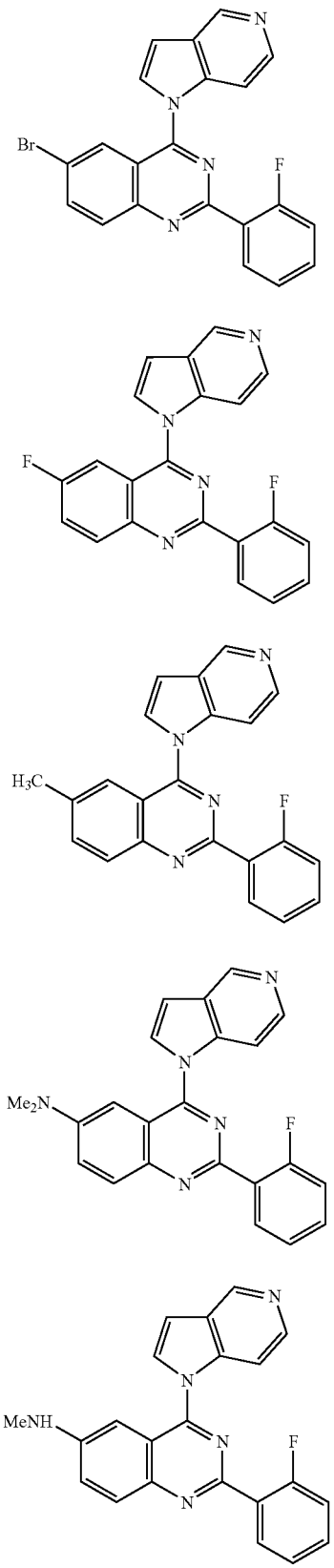
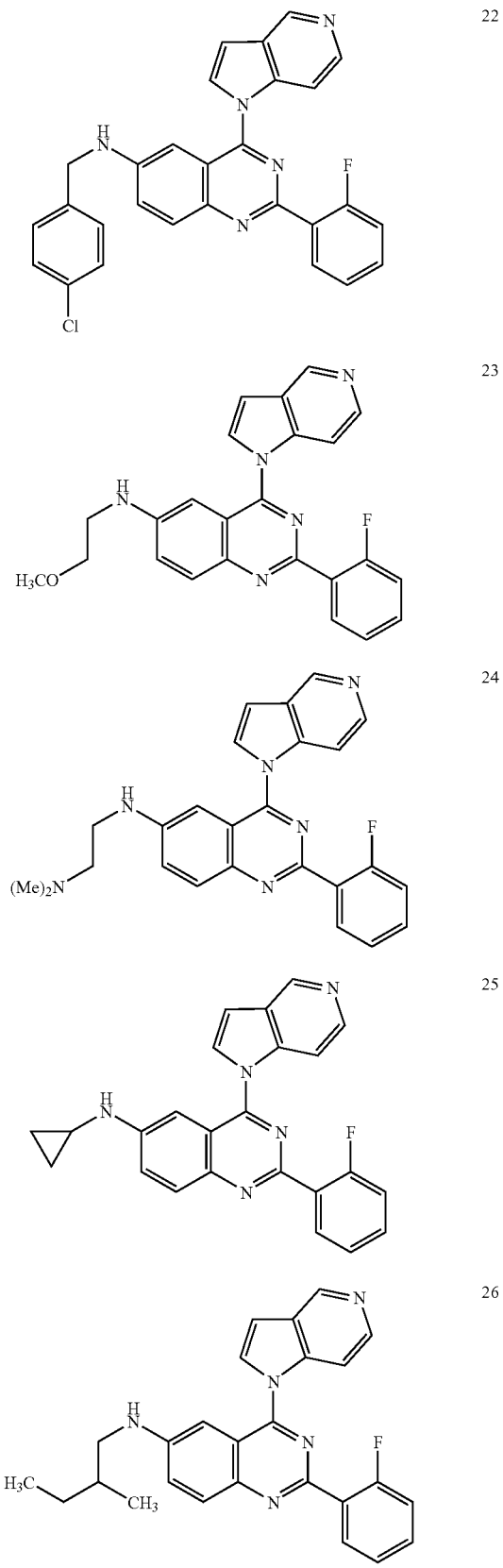

TABLE 1-continued
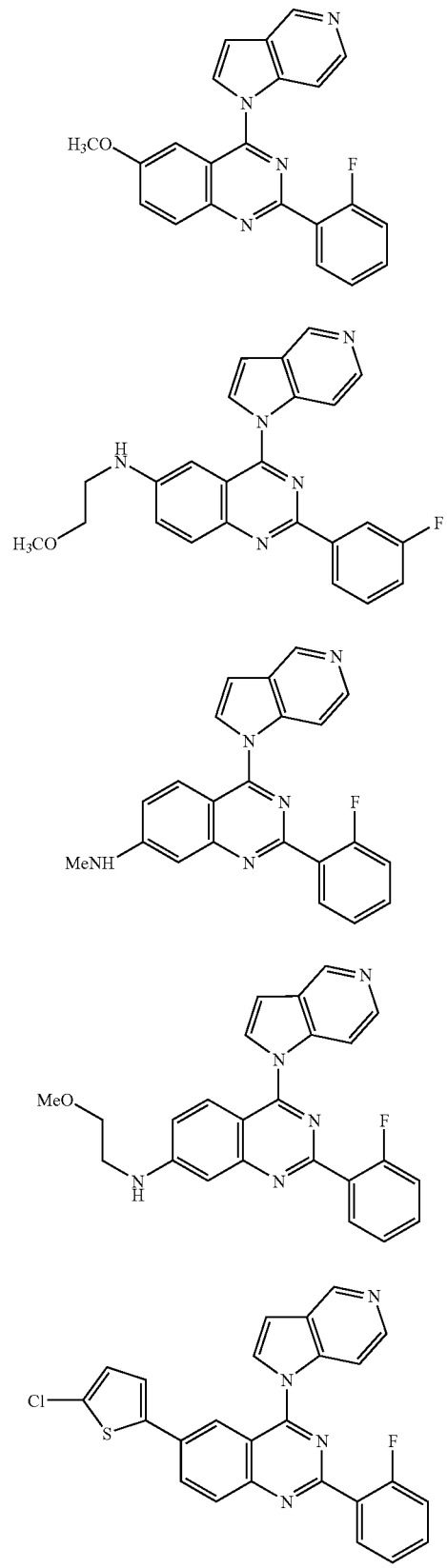
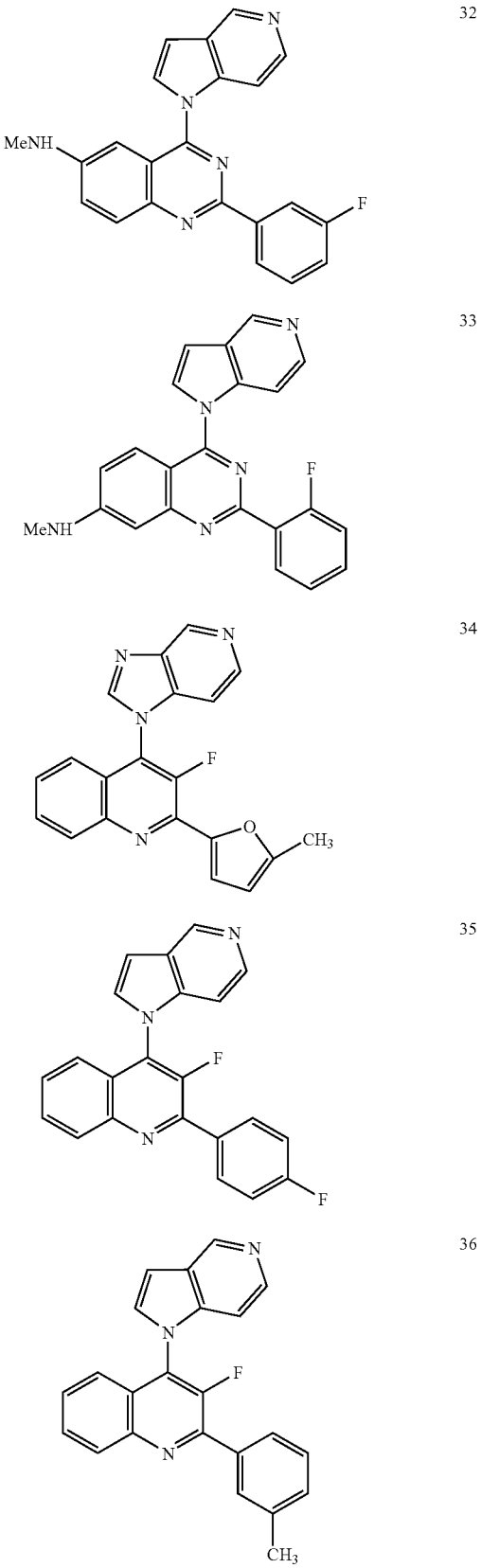

TABLE 1-continued
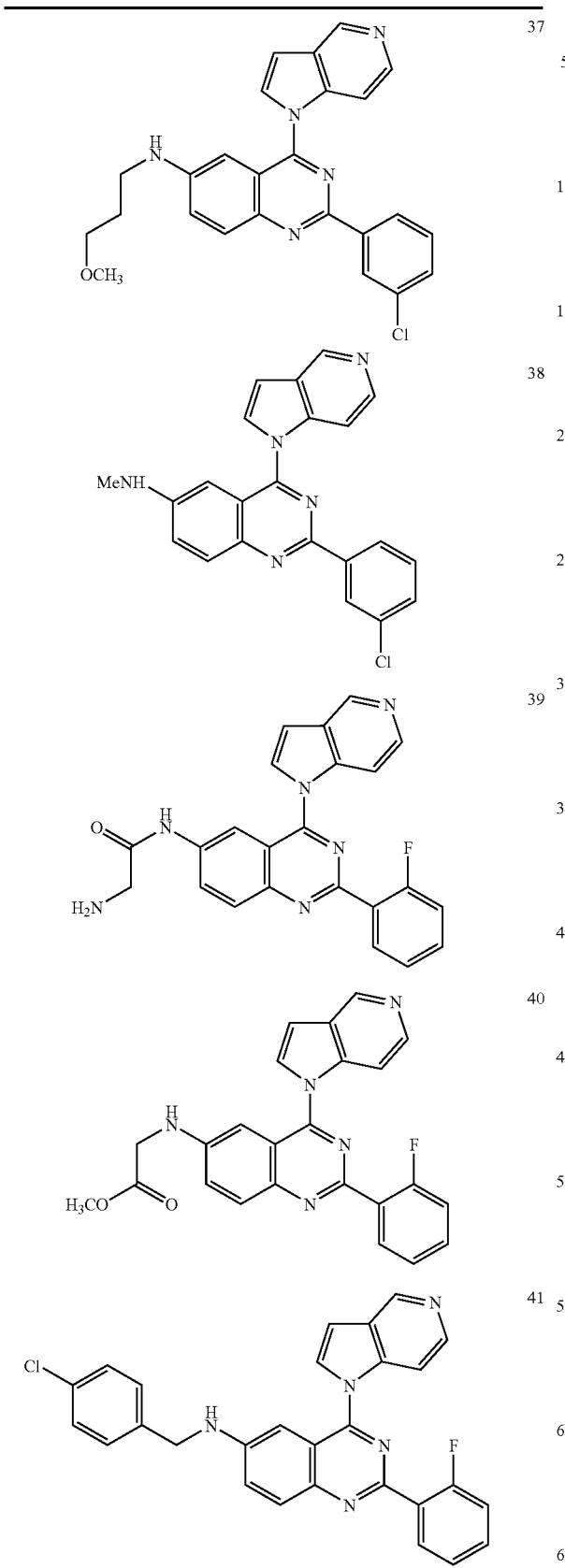
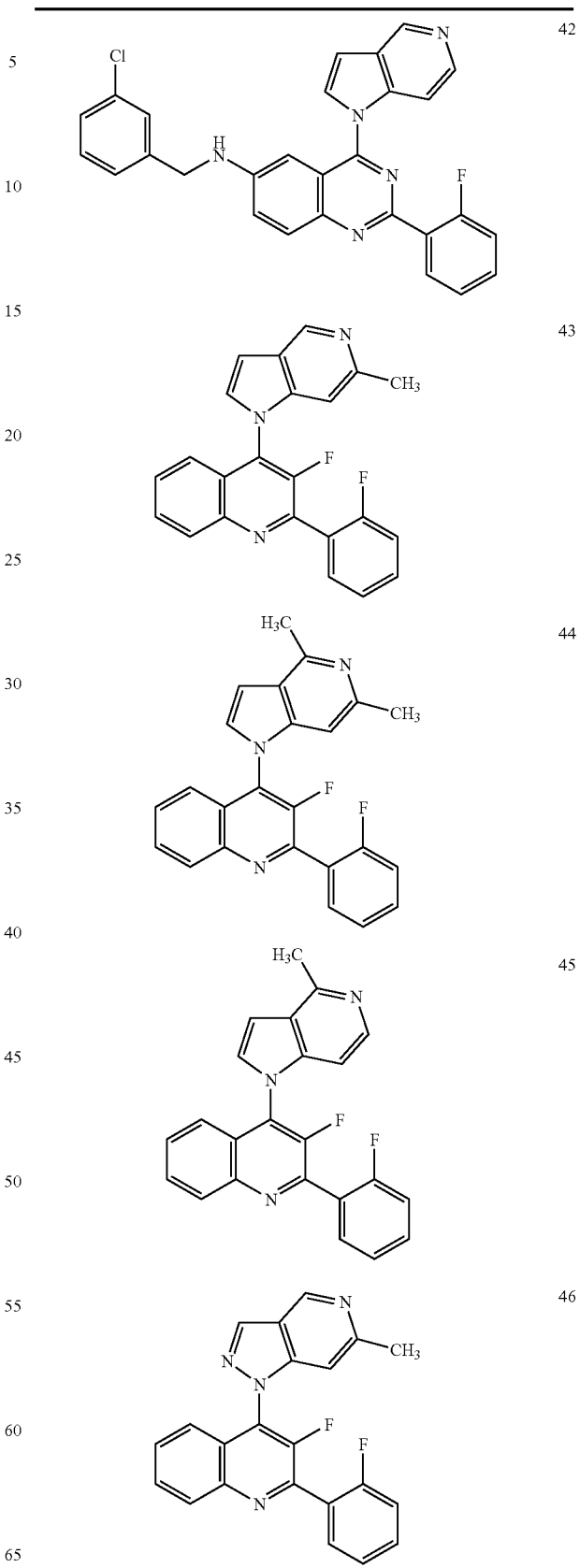

TABLE 1-continued

| | |
|---|---|
| 47 | 52 |
| 48 | 53 |
| 49 | 54 |
| 50 | 55 |
| 51 | 56 |

TABLE 1-continued
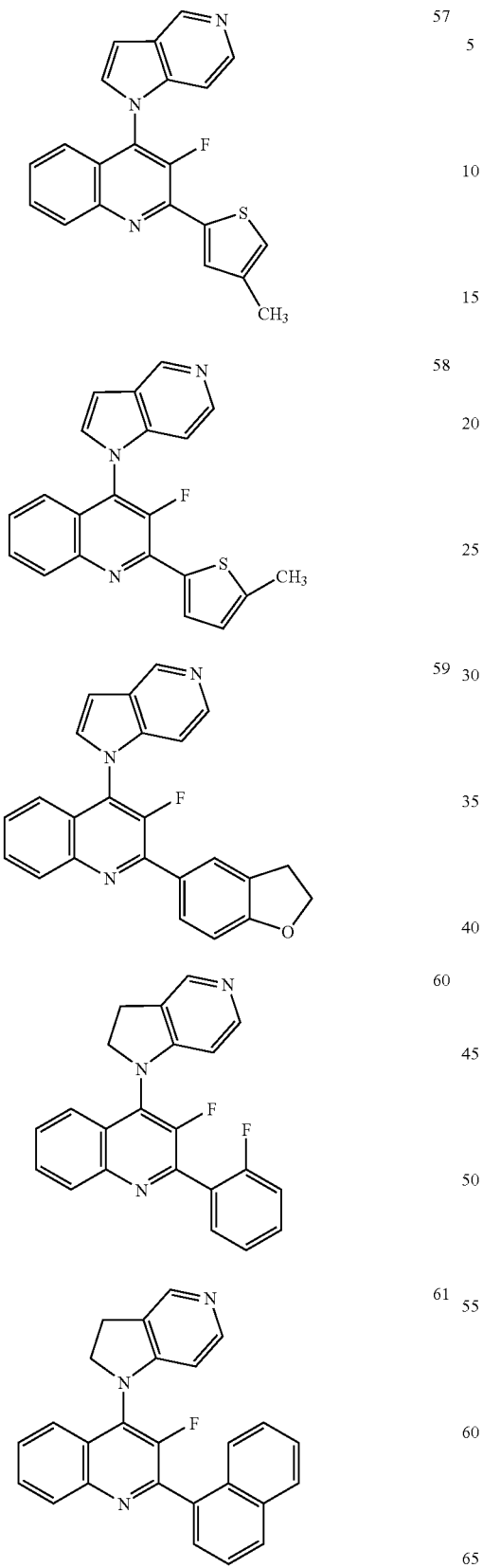
TABLE 1-continued
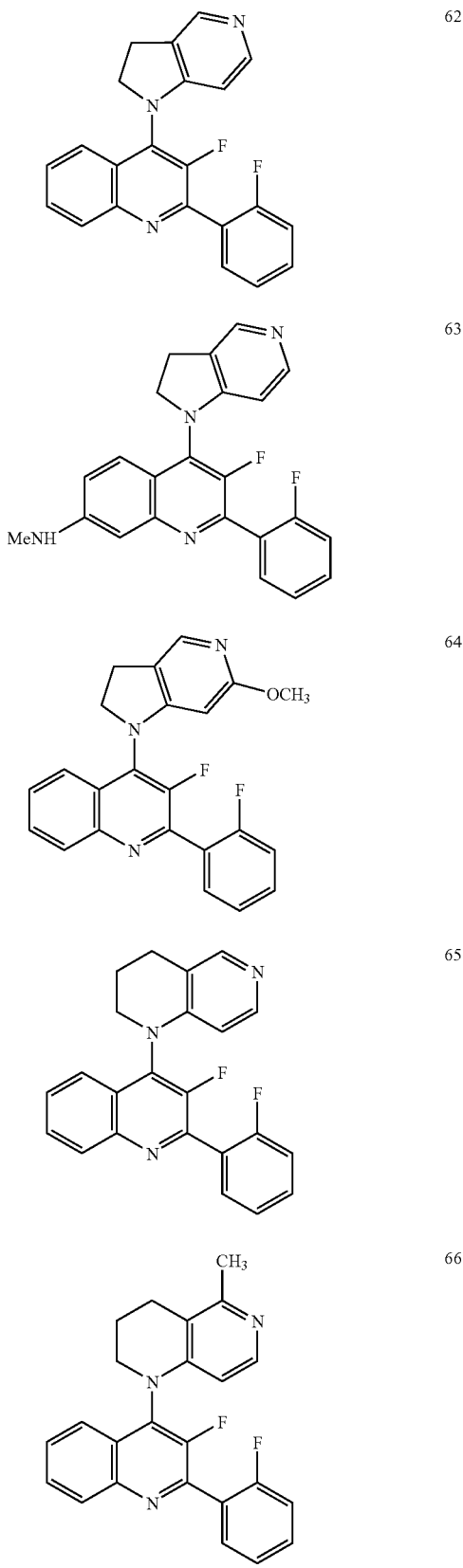

TABLE 1-continued
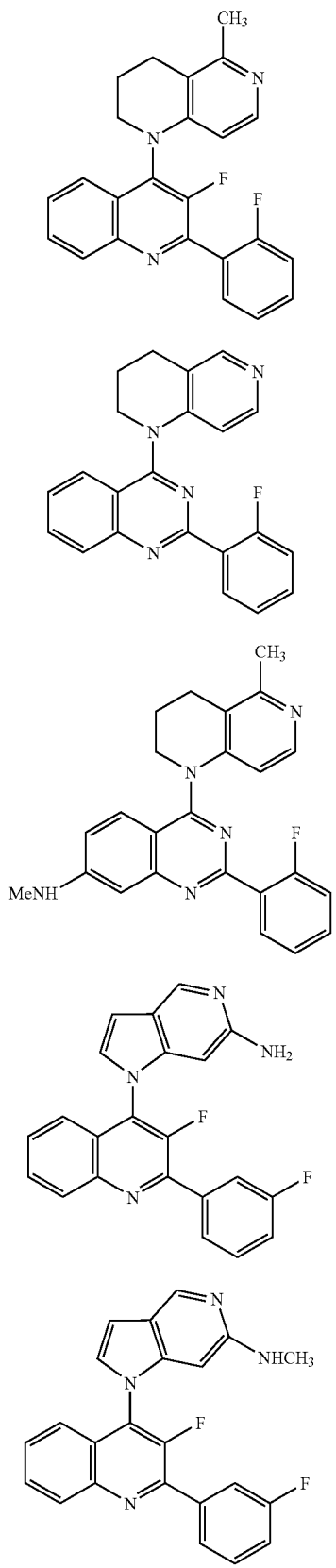
TABLE 1-continued
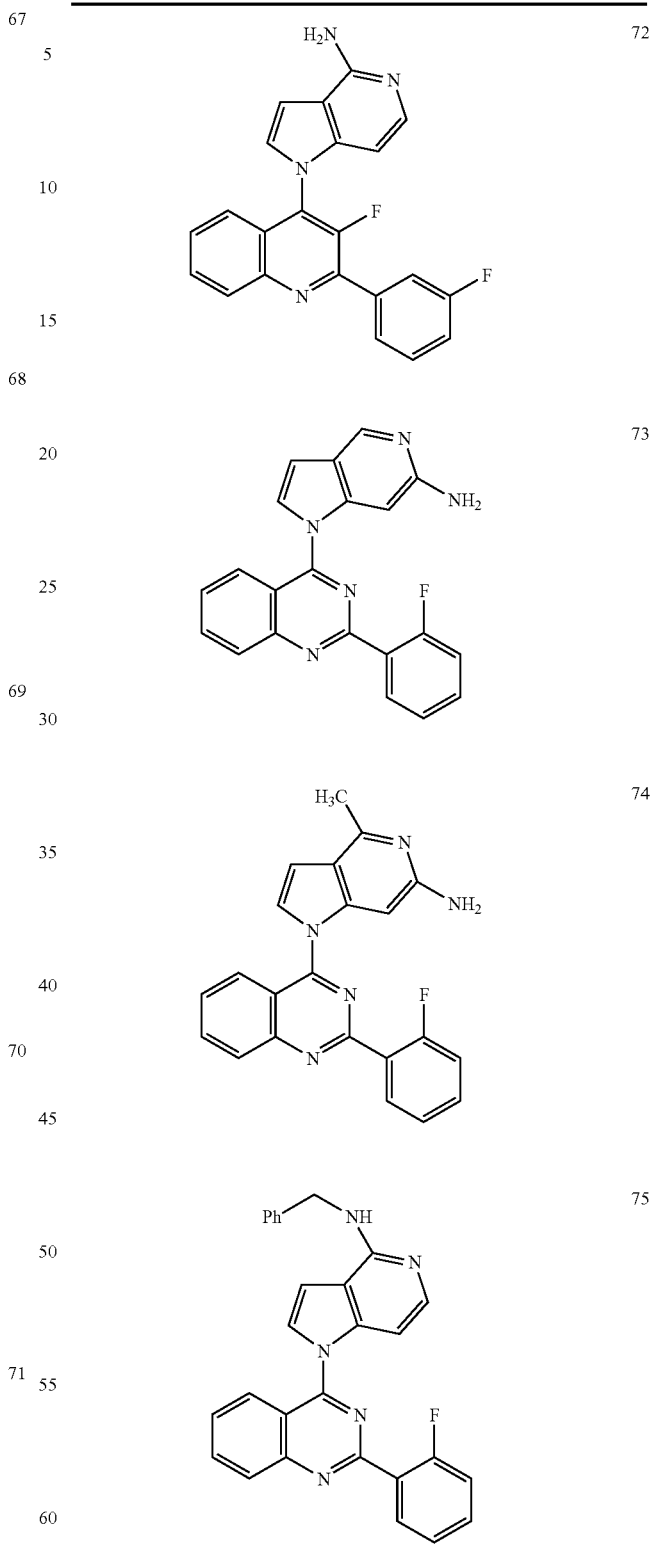
The compounds of this invention may be prepared by methods known to those skilled in the art for analogous compounds, as illustrated by the general schemes below, and by reference to the preparative examples shown below.

Scheme I

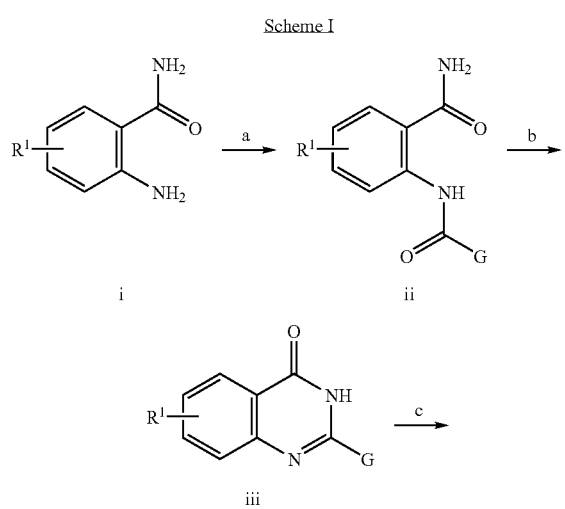

Reagents and conditions: a) Pyridine, G-COCl, CH$_2$Cl$_2$; b) NaOH, ethanol; c) SOCl$_2$, DMF(cat), CHCl$_3$; d) Cs$_2$CO$_3$, DMF.

Scheme I above shows a synthetic route for preparing compounds of formula I-a.

Scheme II

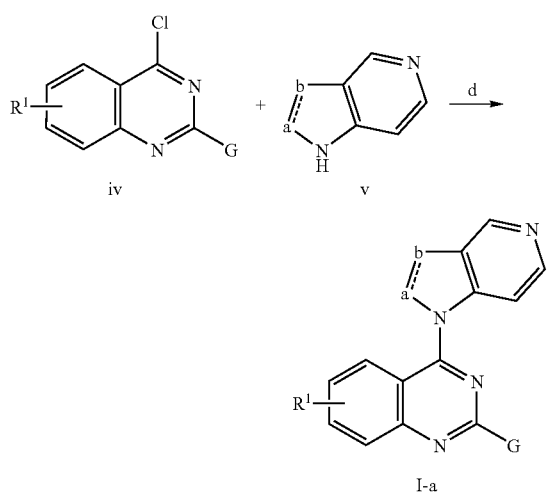

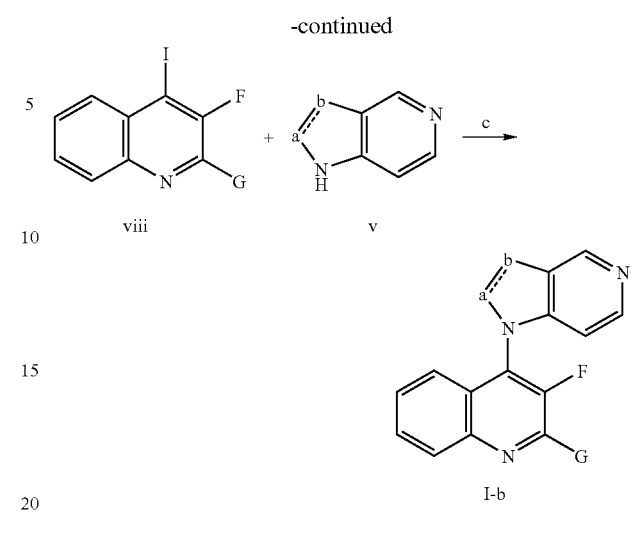

Reagents and conditions: a) G-B(OH)$_2$, THF, H$_2$O, Na$_2$CO$_3$, Pd(PPh$_3$)$_4$; b) LDA, THF, 12; c) Pd$_2$(dba)$_3$, Xantphos, Cs$_2$CO$_3$, THF Scheme II above shows a synthetic route for preparing compounds of formula I-b. The starting 3-fluoro-2-iodoquinoline (vi) is known (Arzel, et al., Tetrahedron Letters (1998), 39(36), 6465–6466). Boronic acid coupling in step (a) introduces the G group at the 2-position of the quinoline to provide intermediate vii. Iodination of vii gives the 3-fluoro-4-iodoquinoline viii, which undergoes palladium-mediated coupling with intermediate v to provide the compounds of formula I-b.

Scheme III

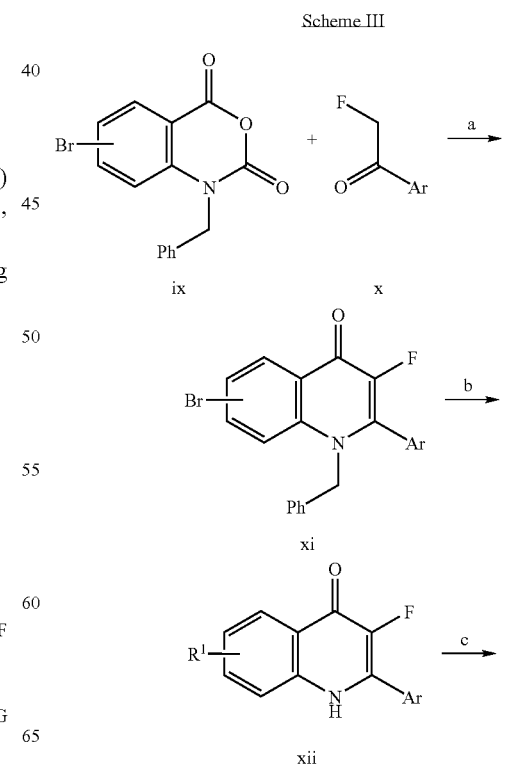

-continued

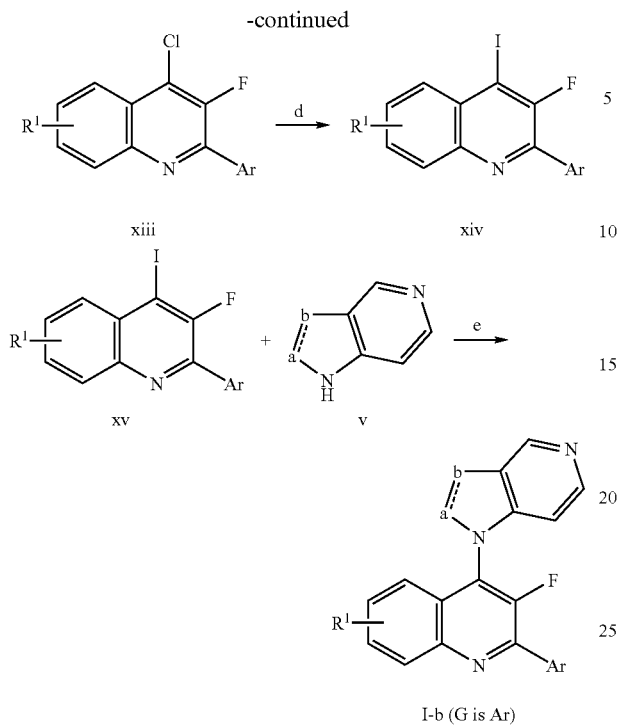

xiii → xiv xv + v → I-b (G is Ar)

Reagents and conditions: (a) NaOMe/MeOH; (b)(i) Pt(S), H₂; (ii) Pd(0), base (c) SOCl₂; (d) nBuLi, then I₂, −30° C.; (e) Cs₂CO₃, DMF.

Scheme III above shows an alternative route for preparing compounds of formula I-b.

Scheme IV

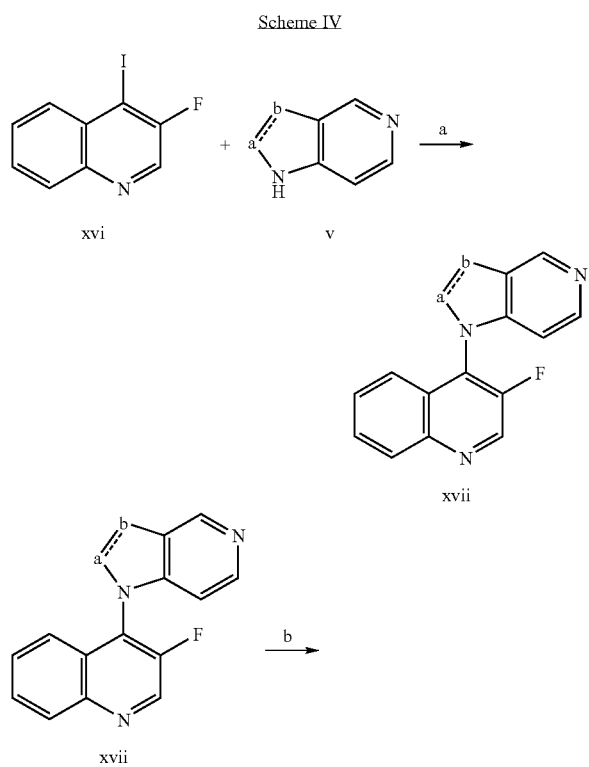

xvi + v → xvii → xvii

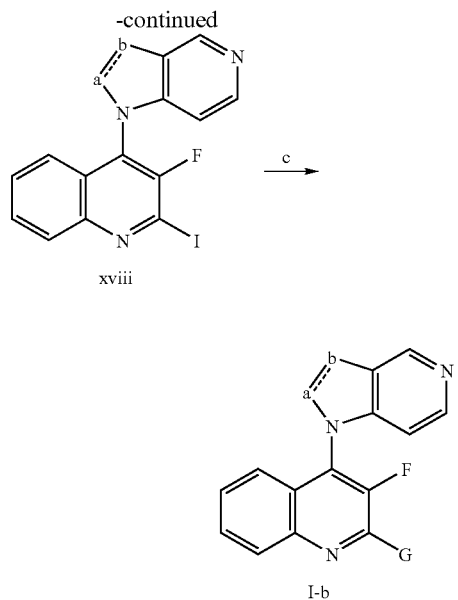

xviii → I-b

Reagents and conditions: a) Pd₂(dba)₃, Xantphos, Cs₂CO₃, THF; b) LDA, THF, 12; c) GB(OH)₂, THF, H₂O, Na₂CO₃, Pd(PPh₃)₄.

Another approach for making compounds of formula I-b is shown in Scheme IV above. The starting 3-fluoro-4-iodoquinoline (xvi) is known (Arzel, et al., Tetrahedron Letters (1998), 39(36), 6465–6466). Palladium-mediated coupling with intermediate v provides compound xvii, which may undergo iodination to provide the 2-iodo compound xviii. Boronic acid coupling in step (c) introduces the G group at the 2-position of the quinoline leading to compounds of formula I-b.

Compounds of the present invention are useful for treating a TGFβ-mediated disease, especially an ALK5-mediated disease. The phrase "TGFβ-condition" or "TGF-β-mediated disease" includes those states, disorders, or diseases characterized by aberrant or undesirable activity or expression of TGFβ. Examples of TGFβ associated disease conditions include, but are not limited to, disorders involving or associated with cardiovascular diseases such as myocardial infarction, stroke, thrombosis, congestive heart failure, dilated cardiomyopathy, myocarditis, or vascular stenosis associated with atherosclerosis, angioplasty treatment, or surgical incisions or mechanical trauma; kidney diseases associated with fibrosis and/or sclerosis, including glomerulonephritis of all etiologies, diabetic nephropathy, and all causes of renal interstitial fibrosis, including hypertension, complications of drug exposure, such as cyclosporin, HIV-associated nephropathy, transplant nephropathy, chronic ureteral obstruction; hepatic diseases associated with excessive scarring and progressive sclerosis, including cirrhosis due to all etiologies, disorders of the biliary tree, and hepatic dysfunction attributable to infections such as hepatitis virus or parasites; syndromes associated with pulmonary fibrosis with consequential loss of gas exchange or ability to efficiently move air into and out of the lungs, including adult respiratory distress syndrome, idiopathic pulmonary fibrosis, or pulmonary fibrosis due to infectious or toxic agents such as smoke, chemicals, allergens, or autoimmune disease; all collagen vascular disorders of a chronic or persistent nature including progressive systemic sclerosis, polymyositis, scleroderma, dermatomyositis, Raynaud's syndrome, or arthritic conditions such as rheumatoid arthritis; eye diseases associated with fibroproliferative states, including proliferative vitreoretinopathy of any etiology or fibrosis associated with ocular surgery such as retinal reattachment, cataract extraction, or drainage procedures of any kind; excessive or hypertrophic scar formation in the dermis occurring during wound healing resulting from trauma or surgical wounds; disorders of the gastrointestinal tract associated with chronic inflammation, such as Crohn's disease or ulcerative colitis or adhesion formation as a result of trauma or surgical wounds, polyposis or states post polyp surgery; chronic scarring of the peritoneum associated with endometriosis, ovarian disease, peritoneal dialysis, or surgical wounds; neurological conditions characterized by TGFβ production or enhanced sensitivity to TGFβ, including states post-traumatic or hypoxic injury, Alzheimer's disease, and Parkinson's disease; and diseases of the joints involving scarring sufficient to impede mobility or produce pain, including states post-mechanical or surgical trauma, osteoarthritis and rheumatoid arthritis.

The TGFβ inhibition activity is useful in treating fibroproliferative diseases, treating collagen vascular disorders, treating eye diseases associated with a fibroproliferative condition, venting excessive scarring, treating neurological conditions and other conditions that are targets for TGFβ inhibitors and in preventing excessive scarring that elicits and accompanies restenosis following coronary angioplasty, cardiac fibrosis occurring after infarction and progressive heart failure, and in hypertensive vasculopathy, and keloid formation or hypertrophic scars occurring during the healing of wounds including surgical wounds and traumatic lacerations. Neurological conditions characterized by TGFβ production include CNS injury after traumatic and hypoxic insults, Alzheimer's disease, and Parkinson's disease.

Other conditions that are potential clinical targets for TGFβ inhibitors include myelofibrosis, tissue thickening resulting from radiation treatment, nasal polyposis, polyp surgery, liver cirrhosis, and osteoporosis. The modulation of the immune and inflammation systems by TGFβ includes stimulation of leukocyte recruitment, cytokine production, and lymphocyte effector function, and inhibition of T-cell subset proliferation, B-cell proliferation, antibody formation, and monocytic respiratory burst. Wahl et al., *Immunol Today* 10:258–61 (1989). TGFβ plays an important role in the pathogenesis of lung fibrosis which is a major cause of suffering and death seen in pulmonary medicine based upon its strong extracellular matrix inducing effect. The association of TGFβ with human lung fibrotic disorders has been demonstrated in idiophatic pulmonary fibrosis, autoimmune lung diseases and bleomycin induced lung fibrosis. Nakao et al., *J. Clin. Inv.*, 104(1):5–11 (1999).

TGFβ is a stimulator for the excess production of extracellular matrix proteins, including fibronectin and collagen. It also inhibits the production of enzymes that degrade these matrix proteins. The net effect is the accumulation of fibrous tissue which is the hallmark of fibroproliferative diseases. Accordingly, one embodiment of this invention relates to a method for inhibiting matrix formation in a patient, comprising administering to the patient a therapeutically effective amount of a compound of formula I.

TGFβ is also an important mediator of diabetic nephropathy, a common complication in patients with either type 1 or type 2 diabetes mellitus. Ziyadeh et al., *Proc. Natl. Acad. Sci.*, 97(14):8015–8020 (2000) evaluated the role of renal TGFβ in the development of chronic structural and functional changes of diabetic nephropathy by assessing the response of db/db mice to chronic treatment with neutralizing anti-TGFβ1 and generalized (tubular and glomerular) up-regulation of TGFβ type II receptor. The antibody effectively prevented increases in renal expression of matrix genes including type IV collagen and fibronectin and may have also stimulated matrix degradative pathways because TGFβ suppresses the activity of metalloproteinases and increase the expression of protease inhibitors such as plasminogen activator inhibitor-1 (PAI-1).

Other TGFβ disease states include inhibition of the intracellular signaling pathway such as fibroproliferative diseases, including kidney disorders associated with unregulated TGFβ activity and excessive fibrosis, including glomerulonephritis (GN), such as mesangial proliferative GN, immune GN, and crescentic GN. Other renal conditions which can be treated by inhibitors of TGFβ intracellular signaling pathway include diabetic nephropathy, renal interstitial fibrosis, renal fibrosis in transplant patients receiving cyclosporin, and HIV-associated nephropathy. Collagen vascular disorders which can be treated by inhibitors of TGFβ intracellular signaling pathway include progressive systemic sclerosis, polymyositis, scleroderma, dermnatomyositis, eosinophilic fascitis, morphea, or those associated with the occurrence of Raynaud's syndrome. Lung fibroses resulting from excessive TGFβ activity include adult respiratory distress syndrome, idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis. Eye diseases associated with a fibroproliferative condition include retinal reattachment surgery accompanying proliferative vitreoretinopathy, cataract extraction with intraocular lens implantation, and post glaucoma drainage surgery.

One embodiment of this invention relates to a method of treating or preventing chronic renal disease, acute renal disease, wound healing, arthritis, osteoporosis, kidney disease, congestive heart failure, ulcers, ocular disorders, corneal wounds, diabetic nephropathy, impaired neurological function, Alzheimer's disease, trophic conditions, atherosclerosis, peritoneal and sub-dermal adhesion.

Another embodiment of this invention relates to the treatment of occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life threatening thrombi occurring throughout the microvasculature leading to widespread organ failure, hemmorhagic stroke, renal dialysis, blood oxygenation and cardiac catherization.

The present compounds are particularly useful for treating an ALK5-mediated disease or condition. ALK5-mediated disease states, include, but are not limited to, chronic renal disease, acute renal disease, wound healing, arthritis, osteoporosis, kidney disease, congestive heart failure, ulcers, ocular disorders, corneal wounds, diabetic nephropathy, impaired neurological function, Alzheimer's disease, trophic conditions, atherosclerosis, any disease wherein fibrosis is a major component, including, but not limited to peritoneal and sub-dermal adhesion, lung fibrosis and liver fibrosis, and restenosis. Compounds of this invention are particularly useful for treating liver fibrosis and kidney fibrosis.

The compounds of this invention are also useful for coating stent devices. Stents have been shown to reduce restenosis, but are thrombogenic. A strategy for reducing the thrombogenicity of stents is to coat, embed, adsorb or covalently attach a thrombin-inhibiting agent to the stent surface. The compounds of the present invention may be used for this purpose. Compounds of the invention may be attached to, or embedded within soluble and/or biodegradeable polymers that are suitable for coating a stent. Examples of such polymers include polyvinylpyrrolidone, polyhydroxy-propylmethacrylamide-phenol, polyhydroxyethyl-aspartamide-phenol, or polyethyleneoxide-polylysine substituted with palmitoyl residues, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels. See European Application 761 251, European Application 604,022, Canadian Patent 2,164,684 and PCT Published Applications WO 96/11668, WO 96/32143 and WO 96/38136.

Compounds and pharmaceutical compositions suitable for use in the present invention include those wherein the active ingredient is administered in an effective amount to achieve its intended purpose. More specifically, a "therapeutically effective amount" means an amount effective to inhibit development of, or to alleviate the existing symptoms of, the subject being treated. Determination of the effective amount is well within the capability of those skilled in the art, especially in light of the detailed disclosure provided herein. A "therapeutically effective dose" refers to that amount of the compound that provides the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio of $LD_{50}$ to $ED_{50}$. Compounds that exhibit high therapeutic indices (i.e., a toxic dose that is substantially higher than the effective dose) are preferred. The data obtained can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized. The exact formulation, route of administration, and dosage is chosen by the individual physician in view of the patient's condition. Dosage amount and interval can be adjusted individually to provide plasma levels of the active compound that are sufficient to maintain desired therapeutic effects.

One embodiment of this invention relates to a composition comprising a compound of formula I or a pharmaceutically acceptable salt thereof, and a pharmaceutically acceptable carrier. It will be appreciated that the compounds of formula I in this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the compounds of formula I, similar to the metabolically labile esters or carbamates, which are capable of producing the parent compounds of formula I in vivo, are within the scope of this invention.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In order that this invention be more fully understood, the following preparative and testing examples are set forth. These examples are for the purpose of illustration only and are not to be construed as limiting the scope of the invention in any way.

SYNTHETIC EXAMPLES

Example 1

Preparation of 2-(2-Fluoro-phenyl)-4-pyrrolo[3,2-c]pyridin-1-yl-quinazoline

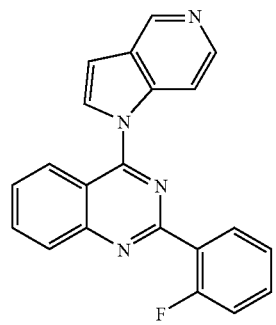

Step A: Preparation of 2-(2-fluorobenzoyl)-amino-benzamide

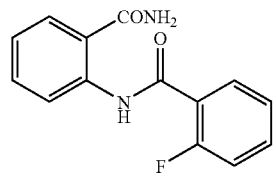

2-Amino-benzamide (1 g, 7.3 mmol) was dissolved in chloroform (25 ml) in a 50 ml round bottomed flask and cooled to 0° C. Pyridine (0.6 ml, 7.3 mmol) was added followed by 2-fluoro-benzoyl chloride (1 ml, 8 mmol) and the mixture was magnetically stirred for 1 hr at this temperature. 10% Hydrochloric acid (50 ml) was added and the precipitated solid was filtered, washed with water and dried to yield pure title compound (1.56 g, 82%).

Step B: Preparation of 2-(2-Fluoro-phenyl)-3H-quinazolin-4-one

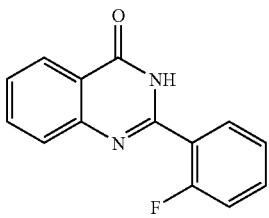

2-(2-fluorobenzoyl)-amino-benzamide from Step A (1.56 g, 6 mmol) was suspended in ethanol (10 ml) in a 50 ml round bottomed flask and to it was added sodium hydroxide (0.92 g, 23 mmol) in 1 ml water and the mixture heated to 80° C. for 1 hr. The ethanol was removed by evaporation and the residue was brought to pH 2 by drop wise addition of conc. hydrochloric acid. The solid was filtered and dried to yield the title compound (0.86 g, 61%). MS (ES) 241.1 (M+H)+

Step C: Preparation of 4-Chloro-2-(2-fluoro-phenyl)-quinazoline

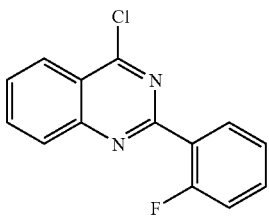

2-(2-Fluoro-phenyl)-3H-quinazolin-4-one from Step B (0.86 g, 3.5 mmol) was suspended in chloroform in a 50 ml round bottomed flask equipped with magnetic stirrer. The flask was cooled to 0° C. and to it was added thionyl chloride (1.2 ml) drop wise followed by N,N-dimethylformamide (0.01 ml) and the mixture heated to 80° C. for 4 hrs. The solvent was removed by evaporation in a rotary evaporator to leave a title compound as a solid (0.68 g, 73%). MS (ES) 259.1 (M+H)+

Step D: Preparation of Title Compound

4-Chloro-2-(2-fluoro-phenyl)-quinazoline from Step C (0.1 g, 0.38 mmol) was dissolved in N,N-dimethylformamide (1 ml) and to it was added 1H-pyrrolo[3,2-c]pyridine (0.046 g, 0.38 mmol) followed by cesium carbonate (0.134 g, 0.41 mmol). The mixture was magnetically stirred and heated to 100° C. for 0.5 hr. The solvent was removed and title compound was obtained pure after column purification on a HPLC reverse phase column, using a water and acetonitrile gradient containing 0.1% trifluoroacetic acid to yield (0.072 g, 56%). MS (ES) 340.1 (M+H)+

Example 2

Preparation of 4-(2,3-Dihydro-pyrrolo[3,2-c]pyridin-1-yl)-2-(2-fluoro-phenyl)-quinazoline

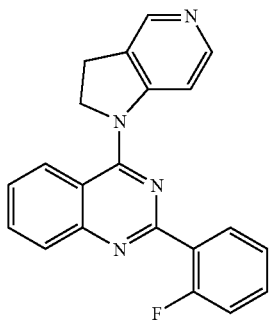

4-Chloro-2-(2-fluoro-phenyl)-quinazoline from Step C example 1 (0.04 g, 0.15 mmol) was dissolved in N,N-dimethylformamide (0.5 ml) and to it was added 2,3-dihydro-1H-pyrrolo[3,2-c]pyridine (0.02 g, 0.16 mmol) followed by cesium carbonate (0.12 g, 0.36 mmol). The mixture was magnetically stirred at room temperature for 0.5 hr. The solvent was removed and title compound was obtained pure after column purification on a HPLC reverse phase column, using a water and acetonitile gradient containing 0.1% trifluoroacetic acid to yield (0.01 g, 19%). MS (ES) 343.0 (M+H)+

Example 3

Preparation of [2-(2-Fluoro-phenyl)-4-pyrrolo[3,2-c]pyridin-1-yl-quinazolin-6-yl]-methyl-amine

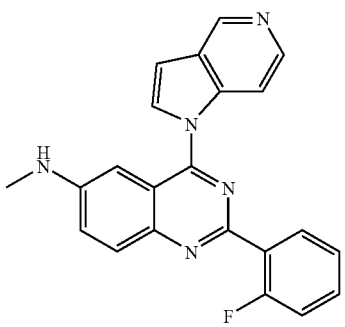

Step A: Preparation of 2-Amino-5-bromo-benzamide

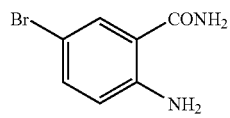

6-Bromo-1H-benzo[d][1,3]oxazine-2,4-dione (5 g, 20 mmol) was suspended in 30 ml of tetrahydrofuran and to it was bubbled NH3 gas for 1.5 hr. The solvent was removed in a rotary evaporator and residue partitioned between methylene chloride and water. The solid was filtered and dried to yield title compound (3.8 g, 85%).

Step B: Preparation of 2-(2-fluorobenzoyl)-amino-5-bromo-benzamide

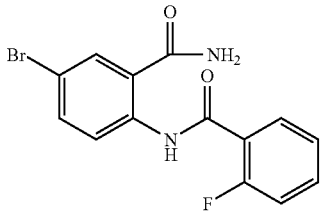

2-Amino-5-bromo-benzamide (2 g, 9.3 mmol) was dissolved in chloroform (40 ml) in a 50 ml round bottomed flask and cooled to 0° C. Pyridine (0.8 ml, 9.3 mmol) was added followed by 2-fluoro-benzoyl chloride (1.3 ml, 10 mmol) and the mixture was magnetically stirred for 1 hr at this temperature. 10% Hydrochloric acid (50 ml) was added and the precipitated solid was filtered, washed with water and dried to yield pure title compound (1.8 g, 57%).

Step C: Preparation of 6-Bromo-2-(2-fluoro-phenyl)-3H-quinazolin-4-one

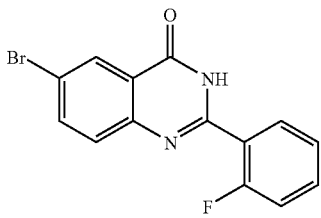

2-(2-fluorobenzoyl)-amino-5-bromo-benzamide from Step B (1.7 g, 5 mmol) was suspended in ethanol (10 ml) in a 50 ml round bottomed flask and to it was added sodium hydroxide (0.4 g, 10 mmol) in 1 ml water and the mixture heated to 80° C. for 1 hr. The ethanol was removed by evaporation and the residue was brought to pH 2 by drop wise addition of conc. hydrochloric acid. The solid was filtered and dried to yield the title compound (1.56 g, 96%). MS (ES) 320.9 (M+H)$^+$ Step D: Preparation of 6-Bromo-4-chloro-2-(2-fluoro-phenyl)-quinazoline

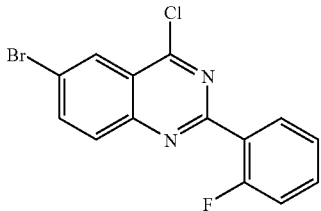

6-Bromo-2-(2-fluoro-phenyl)-3H-quinazolin-4-one from Step C (1.5 g, 4.6 mmol) was suspended in chloroform in a 50 ml round bottomed flask equipped with magnetic stirrer. The flask was cooled to 0° C. and to it was added thionyl chloride (1.6 ml) drop wise followed by N,N-dimethyl formamide (0.01 ml) and the mixture heated to 80° C. for 4 hrs. The solvent was removed by evaporation in a rotary evaporator to leave a title compound as a solid (1.43 g, 90%). MS (ES) 338 (M+H)$^+$ Step E: Preparation of 6-Bromo-2-(2-fluoro-phenyl)-4-pyrrolo[3,2-c]pyridin-1-yl-quinazoline

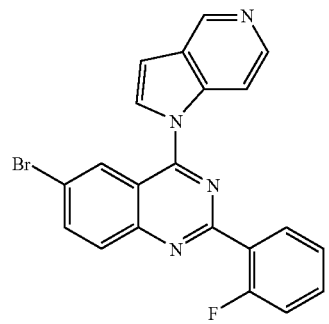

6-Bromo-4-chloro-2-(2-fluoro-phenyl)-quinazoline from Step D (1 g, 2.9 mmol) was dissolved in N,N-dimethyl formamide (3 ml) and to it was added 1H-Pyrrolo[3,2-c]pyridine (0.346 g, 2.9 mmol) followed by cesium carbonate (0.961 g, 2.9 mmol). The mixture was magnetically stirred at room temperature for 1 hr. Water was added and the product filtered to yield title compound (1.236 g, 98%). MS (ES) 420 (M+H)$^+$ Step F: Preparation of [2-(2-Fluoro-phenyl)-4-pyrrolo[3,2-c]pyridin-1-yl-quinazolin-6-yl]-methyl-carbamic acid tert-butyl ester

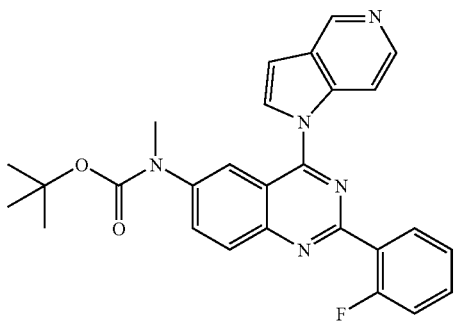

6-Bromo-2-(2-fluoro-phenyl)-4-pyrrolo[3,2-c]pyridin-1-yl-quinazoline from step E (0.1 g, 0.23 mmol) was dissolved in tetrahydrofuran (5 ml) in a 50 ml round bottomed flask. Cesium carbonate (0.11 g, 0.35 mmol), Xanphos (0.007 g, 0.002 mmol) and methyl-carbamic acid tert-butyl ester (0.045 g, 0.35 mmol) was then added. The mixture was degassed for 5 mins and tris (dibenzylidineacetone)dipalladium(0) (0.005 g, 0.005 mmol) was added. The resulting solution was then magnetically stirred and the heated to 80° C. for 3 hrs. Water was added and compound extracted into ethyl acetate, dried over sodium sulfate and concentrated in rotary evaporator to yield desired title compound (0.066 g, 58%). MS (ES) 470.1 (M+H)$^+$ Step G: Preparation of Title Compound

[2-(2-Fluoro-phenyl)-4-pyrrolo[3,2-c]pyridin-1-yl-quinazolin-6-yl]-methylcarbamic acid tert-butyl ester from Step F (0.066 g, 0.14 mmol) was taken in a 25 ml round bottomed flask and to this was added 4N hydrochloric acid in dioxane (0.5 ml) and the mixture magnetically stirred at room temperature for 0.5 hr. The solvent was removed and title compound was obtained pure after column purification on a HPLC reverse phase column, using a water and acetonitrile gradient containing 0.1% trifluoroacetic acid to yield (0.016 g, 30%). MS (ES) 370.1 (M+H)+

Example 4

Preparation of 3-[2-(2-Fluoro-phenyl)-4-pyrrolo[3,2-c]pyridin-1-yl-quinazolin-6-yl]-benzamide

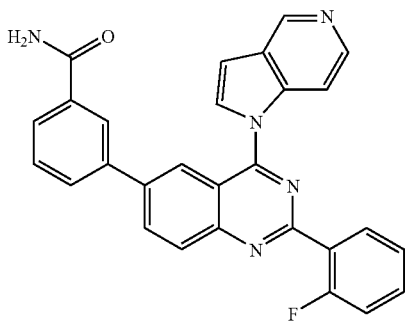

6-Bromo-2-(2-fluoro-phenyl)-4-pyrrolo[3,2-c]pyridin-1-yl-quinazoline from Step E, Example 3 (0.1 g, 0.23 mmol) was dissolved in tetrahydrofuran (5 ml). Sodium carbonate (0.075 g, 0.7 mmol) and benzamide-3-boronic acid (0.040 g, 0.24 mmol) was added followed by tetrakis(triphenylphosphine)palladium(0) (0.005 g, 0.004 mmol) after degassing for 5 mins. Water (0.5 ml) was added drop wise and the mixture was magnetically stirred and heated to 80° C. for 4 hrs. Water was added and product extracted with ethyl acetate. The ethyl acetate layer was dried and evaporated in a rotary evaporator and the residue further purified using a HPLC reverse phase column using an acetonitrile and water gradient containing 0.1% trifluoroacetic acid to yield the title compound (0.028 g, 25%). MS (ES) 460.0 (M+H)+

Example 5

Preparation of 2-(5-Chloro-thiophen-2-yl)-4-(2,3-dihydro-pyrrolo[3,2-c]pyridin-1-yl)-3-fluoro-quinoline Step A: Preparation of 4-(2,3-Dihydro-pyrrolo [3,2-c]pyridin-1-yl)-3-fluoro-quinoline

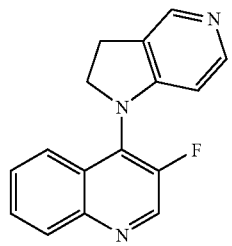

3-Fluoro-4-iodo-quinoline (0.2 g, 0.73 mmol) was placed in a 25 ml round bottomed flask and to it was added tetrahydrofuran (15 ml), xantphos (0.015 g, 0.02 mmol), cesium carbonate (0.476 g, 1.4 mmol), 5-azaindoline (0.087 g, 0.73 mmol). The mixture was degassed for 5 mins. Tris(dibenzylidineacetone) dipalladium(0) (0.0025 g, 0.0025 mmol) was added and the mixture was heated to 80° C. for 48 hrs. Water was and compound extracted into ethyl acetate, dried over sodium sulfate and concentrated in rotary evaporator to yield desired compound (0.132 g, 67%). MS (ES) 266.1 (M+H)+

Step B: Preparation of 4-(2,3-Dihydro-pyrrolo[3,2-c]pyridin-1-yl)-3-fluoro-2-iodo-quinoline

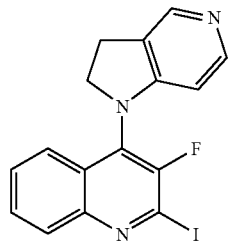

Diisopropylamine (0.052 ml, 0.5 mmol) was added to a 50 ml round bottomed flask containing tetrahydrofuran 15. (5 ml) and magnetically stirred. The flask was cooled to 0° C. and butyllithium (0.146 ml, 2.5M solution in hexane, 0.5 mmol) was added drop wise. After 10 mins the contents were cooled to −78° C. and 4-(2,3-dihydro-pyrrolo[3,2-c]pyridin-1-yl)-3-fluoro-quinoline from Step A (0.100 g, 0.37 mmol) in 20 ml of tetrahydrofuran was added over 15 mins. The stirring was continued for an additional 2 hrs, after which iodine (0.086 g, 0.38 mmol) in 10 ml tetrahydrofuran was added. The reaction mixture was maintained at −78° C. for 2 hrs. Water and tetrahydrofuran (5 ml, 1:9) were added. The reaction mixture was diluted with ethyl acetate, washed with water and brine. Purification by column over silica gel gave pure title compound (0.97 g, 65%). MS (ES) 393.1 (M+H)+

Step C: Synthesis of Title Compound

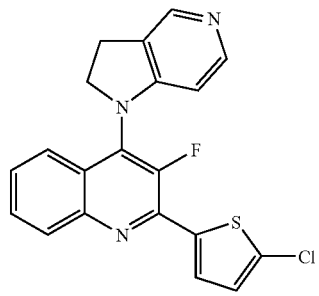

4-(2,3-Dihydro-pyrrolo[3,2-c]pyridin-1-yl)-3-fluoro-2-iodo-quinoline from step B (0.025 g, 0.063 mmol) was dissolved in tetrahydrofuran (5 ml) in a 25 ml round bottomed flask equipped with a magnetic stirrer. Sodium carbonate (0.06 g, 0.1 mmol) was added followed by 5-chlorothiophene-2-boronic acid (0.019 g, 0.08 mmol) and the mixture was degassed for 5 mins. Tetrakis(triphenylphosphine)-palladium(0) (5 mg, 5 mol %) was added followed by 0.5 ml water and the reaction mixture was heated to 80° C. for 4 hrs. The compound was extracted with ethyl acetate, dried and concentrated in vacuo. The title compound was purified by HPLC over a reverse phase column using a gradient of acetonitrile and water containing 0.1% trifluoroacetic acid to yield desired compound (0.012 g, 52%). MS (ES) 482.4 (M+H)+

Assay Methods

The following assay methods were used to evaluate the compounds of the present invention:

Autophosphorylation Assay of GST-ALK5

The cytoplasmic domain of ALK5 was fused to glutathione S-transferase (GST) and the GST-ALK5 fusion protein was expressed in a baculovirus expression system. GST-ALK5 was isolated with glutathione Sepharose 4B beads (Pharmacia Biotech, Sweden) and stored at −80° C. until use.

For detection of GST-ALK5 autophosphorylation and screening of inhibitory compounds, an aliquot of GST-ALK5 in 1× kinase buffer including [$^{33}$P]-γ-ATP was added to 96-well plates in the presence or absence of compounds. The mixture was then incubated at room temperature for 30 min and transferred to each well of a Filterplate with vacuum. The Filterplate was then washed 3 times and radioactivity in each well was counted in a Packard Top-Count.

In Vitro Kinase of HA-ALK5

An expression construct containing full-length ALK5 C-terminally tagged with HA was transfected into COS7 cells, and HA-ALK5 was isolated by immunoprecipitation with anti-HA antibodies. Aliquots of immunoprecipitated HA-ALK5 in 1× kinase buffer plus [$^{33}$P]-γ-ATP was added to 96-well plates in the presence or absence of different concentrations of testing compounds, and incubated at room temperature for 60 min. The reaction mixture was then transferred to a filterplate. The plate was washed three times and radioactivity in each well counted. The $IC_{50}$ value for each compound was determined using the Prism3 program.

ELISA Assay for TGFβ Stimulated Smad2 Phosphorylation

Serum-starved normal human lung fibroblasts (NHLF) in 24-well plate were treated with or without different concentrations of testing compounds for 30 min. The cells were then stimulated with TGFβ for one hour. After fixing, permeabilizing, and blocking, the cells were incubated with phospho-Smad2 specific antibodies followed by HRP-conjugated secondary antibody. The extent of Smad2 phosphorylation was then detected using HRP substrate and read with an ELISA plate reader. $IC_{50}$ for each testing compound was determined using the PRISM3 program.

ELISA Assay for TGFβ Stimulated PAI-1 Secretion

Serum-starved NHLF in 24-well plates were treated with or without different concentrations of testing compounds for 30 min. The cells were then stimulated with TGFβ and incubated in a 37° C. incubator for 24 hours. The media were collected and added to 96-well plates coated with anti-PAI-1 antibodies. The secreted PAI-1 was then detected with another PAI-1 specific antibody followed by HRP-conjugated secondary antibody. The secretion of PAI-1 was detected using HRP substrate and read with an ELISA plate reader. $IC_{50}$ for each testing compound was determined using the PRISM3 program.

SIRCOL Collagen Assay for TGFβ Stimulated Cells

Serum-starved NHLF in 24-well plates were treated with or without different concentrations of testing compounds for 30 min. The cells were then stimulated with TGFβ and incubated for 24 hours. The media were collected and SIRCOL dye reagent was added. After spinning and washing, the pellets were resuspended in alkali reagent and read with an ELISA plate reader. The $IC_{50}$ value for each testing compound was determined using the PRISM3 program.

Detection of TGF-β Stimulated Fibronectin Expression

Serum-starved NHLF in 24-well plates were treated with or without different concentrations of testing compounds for 30 min. The cells were then stimulated with TGFβ and incubated for 24 hours. After washing and fixing, the secreted fibronectin was incubated with fibronectin specific antibodies, followed by incubation with biotin-labeled secondary antibody, streptavidin-peroxidase and HRP substrate. The signal was then detected using an ELISA reader. The $IC_{50}$ value for each testing compound was determined using the PRISM3 program.

The autophosphorylation of GST-ALK5 was developed for primary screening of the compounds that inhibit TGFβ signaling by interacting with ALK5. HA-ALK5 assay is a secondary screening assay to confirm the inhibitory compounds that were selected from the primary screening, and also for the determination of the $IC_{50}$ value for each compound.

P-Smad2, PAI-1, collagen and fibronectin assays are cell-based assays that are used for determination of functional activities of the compounds from the secondary screening. Since the molecules are targets of TGFβ signaling, the data demonstrated that the compounds specifically inhibit TGFβ mediated signal transduction.

Selected compounds were tested in assays for other kinases to determine selectivity for the ALK5 kinase. Other kinases tested included ALK6, p38, FYN as well as the PDGF receptor. Preferred compounds provide an $IC_{50}$ value in the ALK5 assay below 200 nM and are found to be more potent against ALK5 relative to the other kinases tested. Most preferred are compounds that are at least ten times more active against ALK5 than p38 as determined by the $IC_{50}$ value obtained in a standard in vitro inhibition assay.

While we have presented a number of embodiments of this invention, it is apparent that our basic construction can be altered to provide other embodiments which utilize the compounds and methods of this invention. Therefore, it will be appreciated that the scope of this invention is to be defined by the appended claims rather than by the specific embodiments which have been represented by way of example.

The invention claimed is:

1. A compound of formula I:

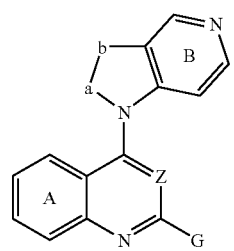

I or a pharmaceutically acceptable salt thereof, wherein:
a-b is wherein each hydrogen is optionally replaced by a $C_{1-4}$ aliphatic group;
Z is N;
G is a phenyl, naphthyl, or 5–6 membered heteroaryl ring having 1–3 ring heteroatoms selected from nitrogen, sulfur or oxygen, wherein G is optionally substituted by 1–3 $R^5$;

Ring A is optionally substituted by 1–3 R$^1$;

Ring B is optionally substituted by 1–2 R$^6$ at a position ortho to the ring nitrogen and is optionally substituted by R$^7$ at the position meta to the ring nitrogen;

each R$^1$ is independently selected from —R$^2$, -T-R$^2$, or —V-T-R$^2$;

each R$^2$ is independently selected from C$_{1-3}$ aliphatic, hydroxy, —N(R$^3$)$_2$, halo, cyano, —OR$^4$, —C(O)R$^4$, —CO$_2$R$^4$, —SR$^4$, —S(O)R$^4$, —S(O)$_2$R$^4$, —N(R$^3$)C(O)R$^4$, —N(R$^3$)CO$_2$R$^4$, —N(R$^3$)SO$_2$R$^4$, —C(O)N(R$^3$)$_2$, —SO$_2$N(R$^3$)$_2$, —N(R$^3$)C(O)N(R$^3$)$_2$, —OC(O)R$^4$, phenyl, 5–6 membered heterocyclyl or 5–6 membered heteroaryl;

each T is independently a C$_{1-5}$ alkylidene that is optionally interrupted by —O—, —C(O)—, —S—, —S(O)—, —S(O)$_2$—, or —N(R$^3$)—;

each V is independently selected from —O—, —S—, —S(O)—, —S(O)$_2$—, —C(O)—, —N(R$^3$)—, —N(R$^3$)C(O)—, or —N(R$^3$)C(O)$_2$—, —N(R$^3$)S(O)$_2$—, —C(O)N(R$^3$)—, —S(O)$_2$N(R$^3$)—, —N(R$^3$)C(O)N(R$^3$)—, or —OC(O)—;

each R$^3$ is independently selected from hydrogen, C$_{1-6}$ aliphatic, —C(O)R$^4$, —C(O)$_2$R$^4$, —SO$_2$R$^4$, or two R$^3$ on the same nitrogen together with their intervening nitrogen form a 5–6 membered heterocyclyl or heteroaryl ring having 1–3 ring heteroatoms selected from nitrogen, oxygen or sulfur;

each R$^4$ is independently selected from a C$_{1-6}$ aliphatic group, phenyl or a 5–6 membered heteroaryl or heterocyclyl having 1–3 ring heteroatoms selected from nitrogen, oxygen or sulfur;

each R$^5$ is independently selected from C$_{1-6}$ aliphatic, halo, —OH, —N(R$^3$)$_2$, cyano, —OR$^4$, —C(O)R$^4$, —CO$_2$R$^4$, —SR$^4$, —S(O)R$^4$, —S(O)$_2$R$^4$, —N(R$^3$)C(O)R$^4$, —N(R$^3$)CO$_2$R$^4$, —N(R$^3$)SO$_2$R$^4$, —C(O)N(R$^3$)$_2$, —SO$_2$N(R$^3$)$_2$, —N(R$^3$)C(O)N(R$^3$)$_2$, —OC(O)R$^4$, —OC(O)N(R$^3$)$_2$, phenyl, 5–6 membered heterocyclyl or 5–6 membered heteroaryl, or two adjacent R$^5$ on a phenyl, naphthyl or heteroaryl ring are taken together with their intervening atoms to form a 5–6 membered fused ring having 0–2 heteroatoms selected from nitrogen, oxygen or sulfur;

each R$^6$ is independently selected from a C$_{1-4}$ alkyl, C$_{1-4}$ alkoxy, or C$_{1-4}$ mono- or dialkylamino; and R$^7$ is selected halo, —OH, —N(R$^3$)$_2$, cyano, —OR$^4$, —C(O)R$^4$, —CO$_2$R$^4$, —SR$^4$, —S(O)R$^4$, —S(O)$_2$R$^4$, —N(R$^3$)C(O)R$^4$, —N(R$^3$)CO$_2$R$^4$, —N(R$^3$)SO$_2$R$^4$, —C(O)N(R$^3$)$_2$, —SO$_2$N(R$^3$)$_2$, —N(R$^3$)C(O)N(R$^3$)$_2$, or —OC(O)R$^4$.

2. The compound according to claim 1 characterized by one or more of the follwing:

(a) G is a phenyl, naphthyl or heteroaryl ring that is unsubstituted or substituted by 1–2 R$^5$ groups;

(b) Ring A is unsubstituted or substituted by 1–2 R$^1$ groups at positions 6 and/or 7 of the quinoline or quinazoline ring system;

(c) Ring B is unsubstituted or substituted by an R$^6$ group where R$^6$ is methyl, amino, or methylamino;

(d) R$^1$ is R$^2$, T-R$^2$ or V-T-R$^3$ where R$^2$ is halo, C$_{1-3}$ aliphatic, C$_{1-3}$ alkoxy, amino, C$_{1-6}$ mono- or dialkylamino, T is a C$_{1-4}$ alkylidene that is optionally interrupted by —C(=O)—, V is —O— or —N(R$^3$)—, and R$^3$ is hydrogen or methyl; and (e) R$^5$ is halo, C$_{1-6}$ alkoxy, C$_{1-6}$ alkyl, C$_{3-6}$ cycloalkyl, haloalkyl, C$_{1-6}$ alkylthio, mono- or dialkylamino, aminocarbonyl, mono- or dialkylaminocarbonyl, C$_{1-6}$ alkylcarbonyl, C$_{1-6}$ alkylsulfonyl, C$_{1-6}$ alkoxycarbonyl, C$_{1-6}$ alkoxycarbonylamino, C$_{1-6}$ alkylcarbonyloxy, C$_{1-6}$ alkylsulfonylamino, mono- or dialkylaminosulfonyl, mono- or dialkylaminocarbonylamino, or two adjacent R$^5$ are taken together with their intervening atoms to form a fused 5–6 membered ring having 0–2 ring heteroatoms.

3. The compound according to claim 2 having the features (a) through (e).

4. A compound selected from the group consisting of:

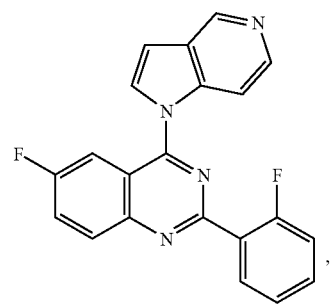

18

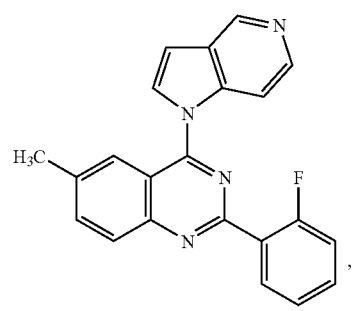

19

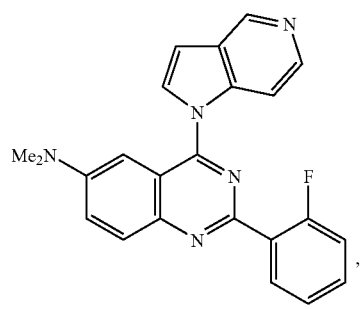

20

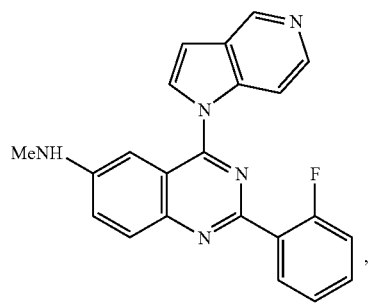

21

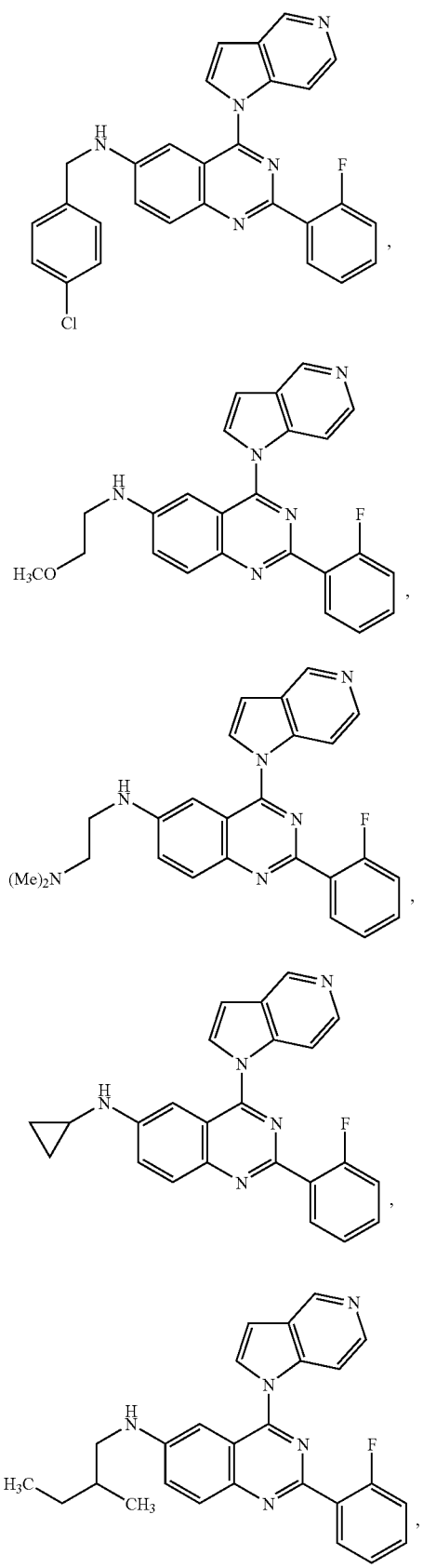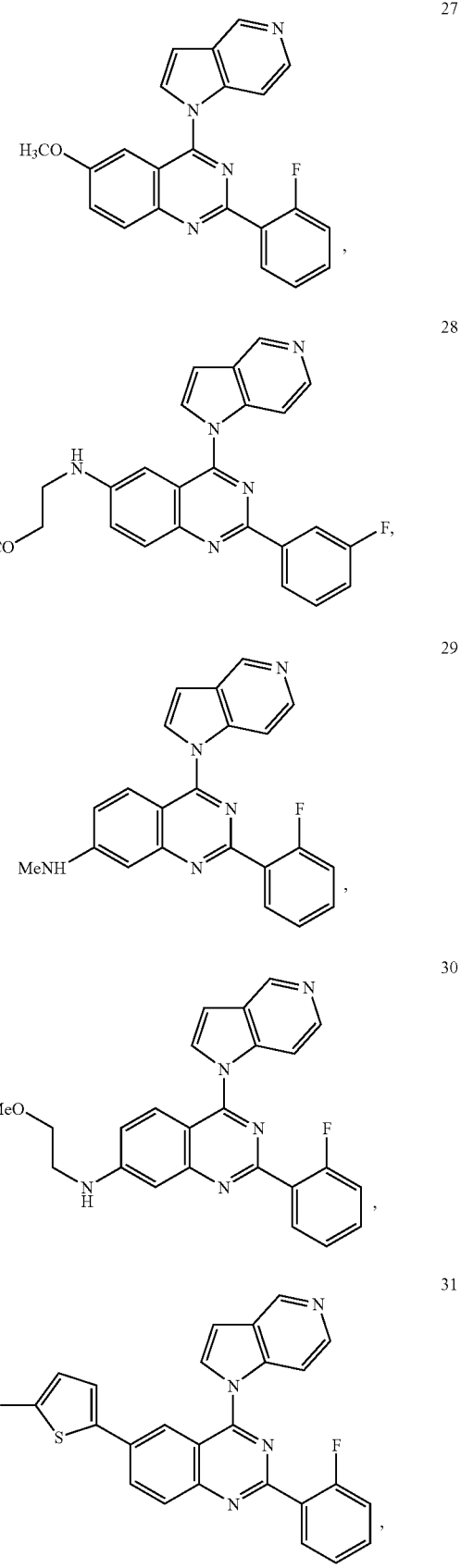

-continued
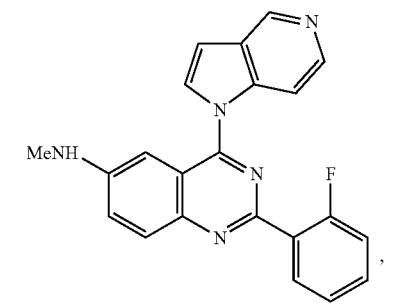
32
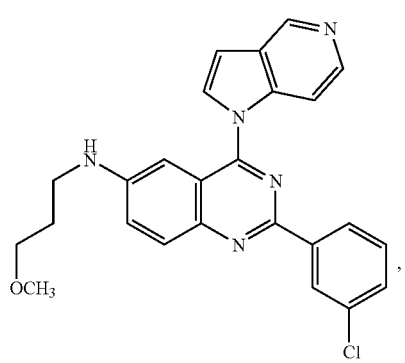
37
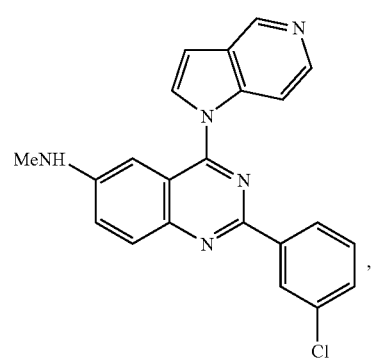
38
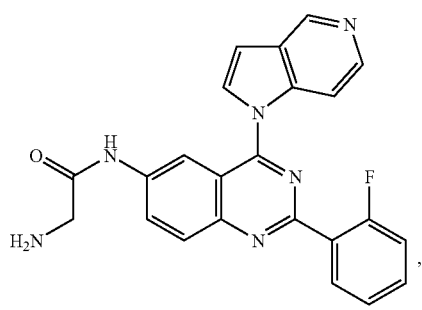
39
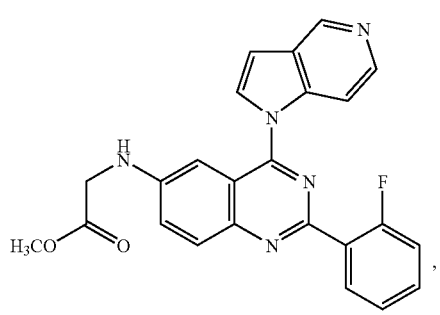
40
-continued
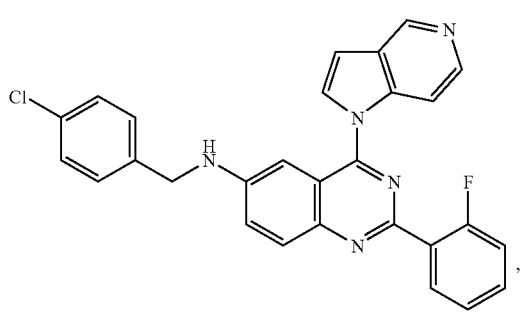
41
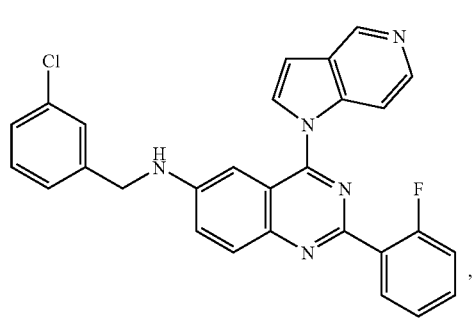
42
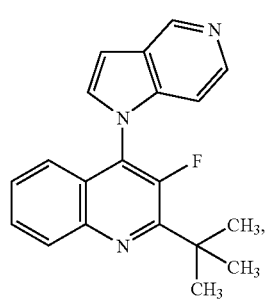
52
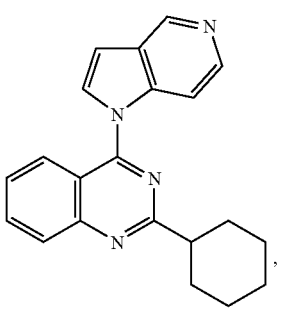
53
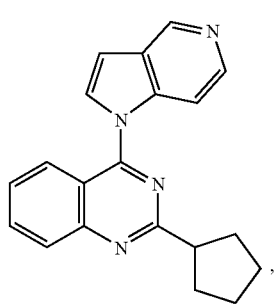
54

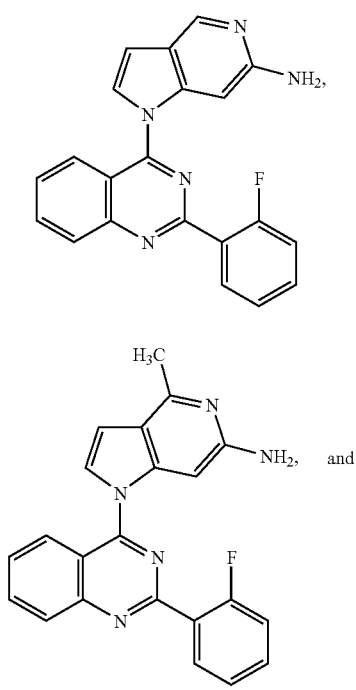

73

74

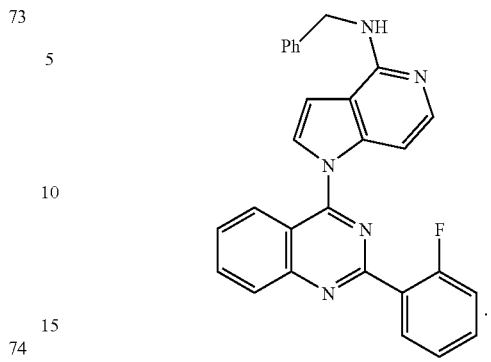

75

5. A pharmaceutical composition comprising a compound according to any of claims 1 or 4 and a pharmaceutically acceptable carrier.

6. A method of treating arthritis in a patient, comprising administering to the patient a therapeutically effective amount of a compound according to claim 1, or a pharmaceutically acceptable salt thereof.

7. A method of treating arthritis in a patient, comprising administering to the patient a therapeutically effective amount of a compound according to claim 4, or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 7,189,733 B2 |
| APPLICATION NO. | : 10/795538 |
| DATED | : March 13, 2007 |
| INVENTOR(S) | : Robert M. Scarborough et al. |

It is certified that error appears in the above-identified patent and that said Letters Patent is hereby corrected as shown below:

IN THE CLAIMS:

In Claim 1, column 44, line 61, immediately following "a-b is," insert the following phrase --CH=CH--.

Signed and Sealed this

Seventh Day of August, 2007

JON W. DUDAS
*Director of the United States Patent and Trademark Office*

UNITED STATES PATENT AND TRADEMARK OFFICE
CERTIFICATE OF CORRECTION

PATENT NO. : 7,189,733 B2
APPLICATION NO. : 10/795538
DATED : March 13, 2007
INVENTOR(S) : Robert M. Scarborough, Anjali Pandey and Meenakshi S. Venkatraman Page 1 of 1

It is certified that error appears in the above-identified patent and that said Letters Patent is hereby corrected as shown below:

Please make the following corrections to the claims:

IN THE CLAIMS:

In Claim 4, column 50, lines 29-40, delete "compound number 52".

Signed and Sealed this
Nineteenth Day of June, 2012

David J. Kappos
*Director of the United States Patent and Trademark Office*